(12) United States Patent
Su et al.

(10) Patent No.: US 7,055,378 B2
(45) Date of Patent: Jun. 6, 2006

(54) SYSTEM FOR WIDE FREQUENCY DYNAMIC NANOMECHANICAL ANALYSIS

(75) Inventors: Chanmin Quanmin Su, Ventura, CA (US); Sergei Magonov, Santa Barbara, CA (US)

(73) Assignee: Veeco Instruments, Inc., Woodbury, NY (US)

( * ) Notice: Subject to any disclaimer, the term of this patent is extended or adjusted under 35 U.S.C. 154(b) by 216 days.

(21) Appl. No.: 10/638,963

(22) Filed: Aug. 11, 2003

(65) Prior Publication Data

US 2005/0034512 A1    Feb. 17, 2005

(51) Int. Cl.
   *G01N 27/00*    (2006.01)
(52) U.S. Cl. .......................................... 73/105
(58) Field of Classification Search .................. 73/105
   See application file for complete search history.

(56) References Cited

U.S. PATENT DOCUMENTS

| | | |
|---|---|---|
| 4,295,374 A | 10/1981 | Kusy |
| 4,418,573 A | 12/1983 | Madigosky et al. |
| 4,506,547 A | 3/1985 | Kunze et al. |
| RE32,457 E | 7/1987 | Matey |
| 5,065,103 A | 11/1991 | Slinkman et al. |
| 5,139,079 A | 8/1992 | Becraft et al. |
| 5,329,808 A | 7/1994 | Elings et al. |
| 5,412,980 A | 5/1995 | Elings et al. |
| 5,519,212 A | 5/1996 | Elings et al. |
| 5,675,075 A | 10/1997 | Arnold et al. |
| 5,700,953 A | 12/1997 | Hlady et al. |
| 5,710,426 A | 1/1998 | Reed et al. |
| 5,764,068 A | 6/1998 | Katz et al. |
| 5,866,807 A | 2/1999 | Elings et al. |
| 5,883,705 A * | 3/1999 | Minne et al. .................. 355/71 |

(Continued)

FOREIGN PATENT DOCUMENTS

JP    2000207612    7/2000

OTHER PUBLICATIONS

Albrecht, Thomas et al. "Microfabrication of Integrated Scanning Tunneling Microscope", J. Vac. Scii. Technol. A vol. 8, n. 1 Jan./Feb. 1990, pp. 317-318.*

(Continued)

*Primary Examiner*—Michael Cygan
(74) *Attorney, Agent, or Firm*—Patterson, Thuente, Skaar & Christensen, P.A.

(57) ABSTRACT

Dynamic nanomechanical analysis of a sample is performed by using a cantilever probe that interacts with the sample using a force applied across a wide range of frequencies that includes frequencies greater than 300 Hz. The motion of the cantilever probe is detected in response to the applied force over the range of frequencies and analyzed over at least a portion of the wide range of frequencies to determine a mechanical response of the sample, preferably including quality factor and modulus of the sample. The analysis of the motion of the cantilever probe is preferably performed in terms of amplitude, phase, and frequency of both the probe and the sample and preferably, where the applied force is analyzed to determine both a real and an imaginary modulus of a mechanical response of the sample. Preferably, the force is applied so as to produce a minimum of phase and amplitude response variation in the absence of the sample. Furthermore the motion of the cantilever can be flexural or torsional and combinations thereof.

27 Claims, 17 Drawing Sheets

Variation of the response phase of the cantilever probe should be less than 10 degree of its average response across entire frequency range ( below 1st harmonics of the cantilever)

U.S. PATENT DOCUMENTS

| | | |
|---|---|---|
| 5,902,928 A | 5/1999 | Chen et al. |
| 5,992,226 A * | 11/1999 | Green et al. ............... 73/105 |
| 6,006,593 A | 12/1999 | Yamanaka |
| 6,008,489 A | 12/1999 | Elings et al. |
| RE36,488 E | 1/2000 | Elings et al. |
| 6,095,679 A | 8/2000 | Hammiche et al. |
| 6,146,013 A | 11/2000 | Huetter et al. |
| 6,172,506 B1 | 1/2001 | Adderton et al. |
| 6,185,991 B1 | 2/2001 | Hong et al. |
| 6,200,022 B1 | 3/2001 | Hammiche et al. |
| 6,297,502 B1 * | 10/2001 | Jarvis et al. ............. 250/307 |
| 6,318,159 B1 | 11/2001 | Chen et al. |
| 6,349,591 B1 | 2/2002 | Fretigny et al. |
| 6,388,452 B1 | 5/2002 | Picciotto |
| 6,445,194 B1 | 9/2002 | Adkisson et al. |
| 6,459,280 B1 | 10/2002 | Bhushan et al. |
| 6,465,267 B1 | 10/2002 | Wang et al. |
| 6,472,236 B1 | 10/2002 | Wang et al. |
| 6,530,266 B1 * | 3/2003 | Adderton et al. ............. 73/105 |
| 6,596,992 B1 * | 7/2003 | Ando et al. ................ 250/306 |
| 6,605,941 B1 * | 8/2003 | Abe .......................... 324/244 |
| 6,877,365 B1 * | 4/2005 | Watanabe et al. ............. 73/105 |
| 6,906,450 B1 * | 6/2005 | Tamayo De Miguel et al. . 310/317 |
| 2002/0102748 A1 | 8/2002 | Kwon |
| 2002/0130674 A1 | 9/2002 | Lagowski et al. |

OTHER PUBLICATIONS

A.P. French, *Vibrations and Waves*, The M.I.T. Introductory Physics Series, Copyright 1971, 1966, pp. 83-84.

* cited by examiner

Variation of the response amplitude of the cantilever probe should be less than 50% of its average response across entire frequency range (below 1st harmonics of the cantilever)

Variation of the response phase of the cantilever probe should be less than 10 degree of its average response across entire frequency range ( below 1st harmonics of the cantilever)

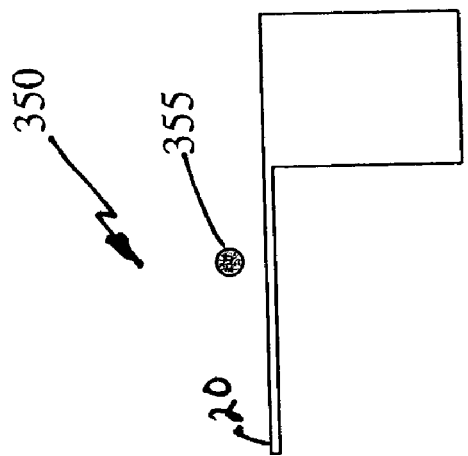
Fig 6(b)
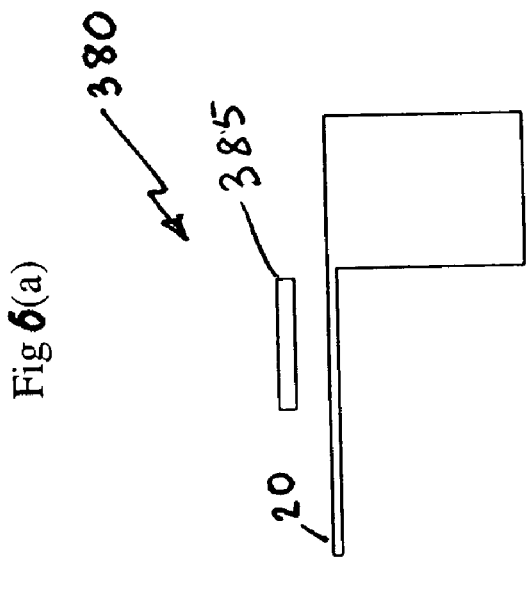
Fig 6(d)
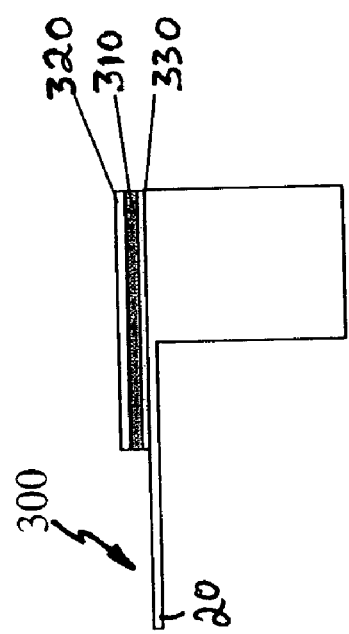
Fig 6(a)
Fig 6(c)

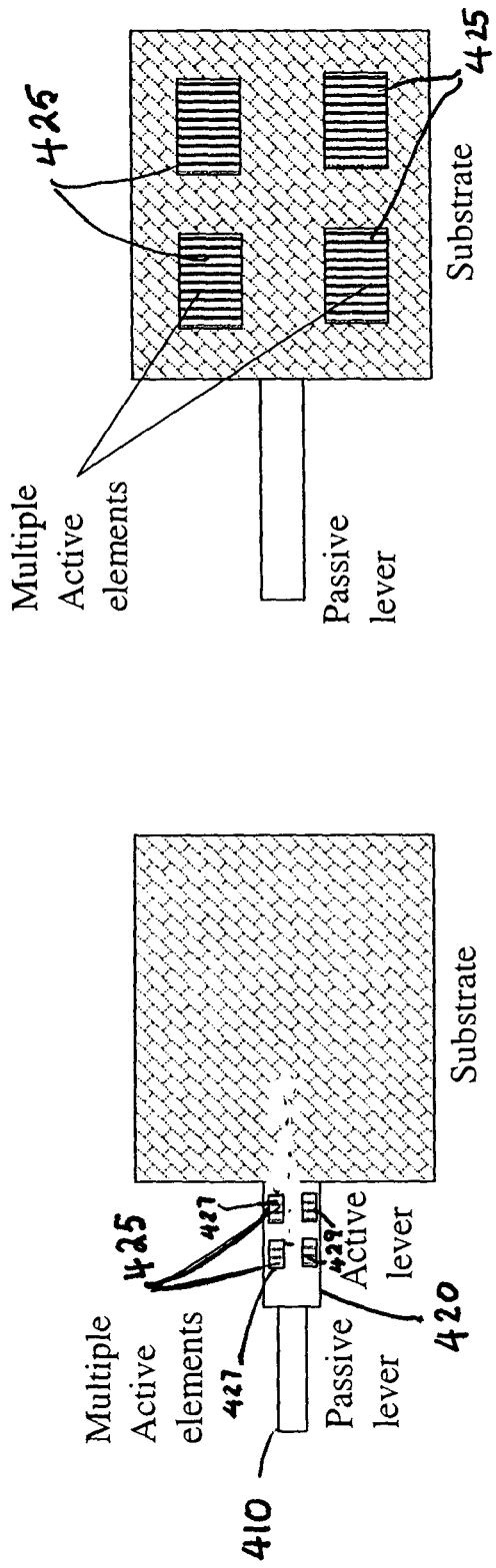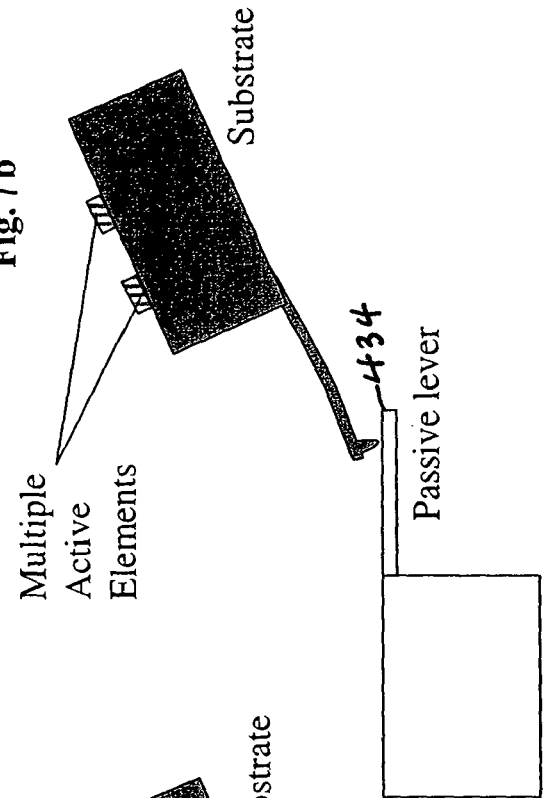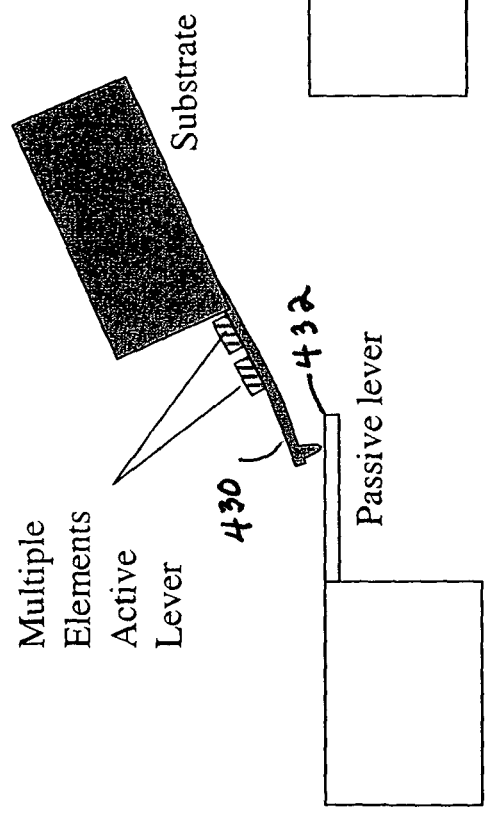
Fig. 7a
Fig. 7b
Fig. 7c
Fig. 7d

Alternative of Measurement Sample
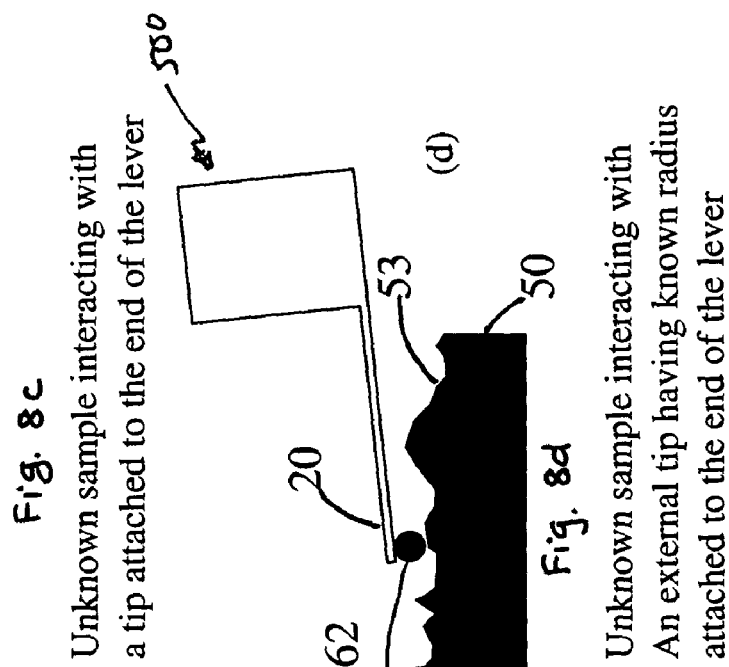
Fig. 8a
Fig. 8b
Unknown sample coated on lever surface
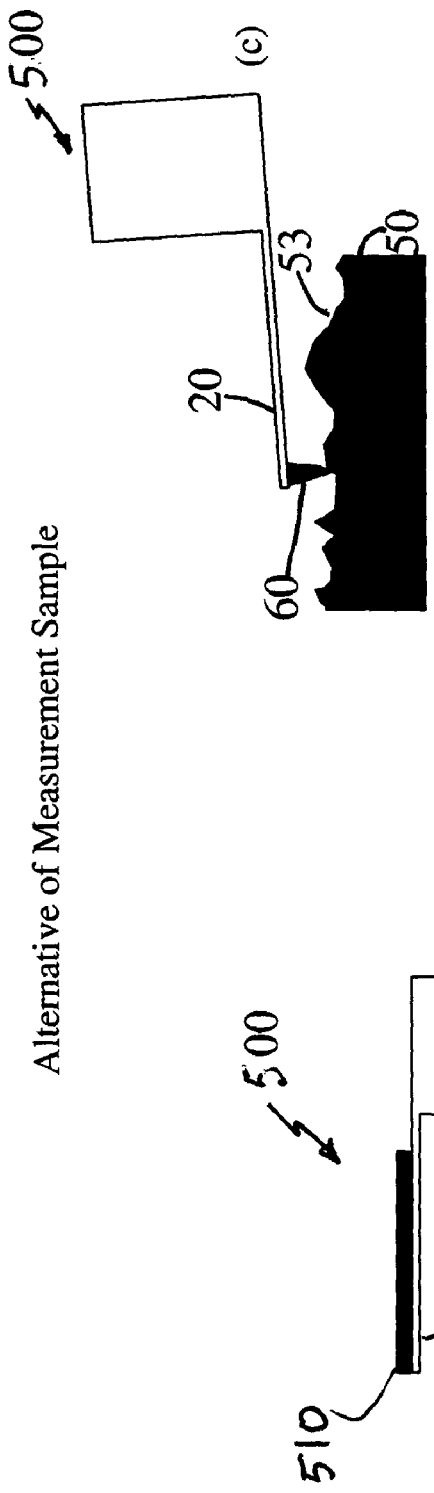
Fig. 8c
Unknown sample interacting with a tip attached to the end of the lever
Fig. 8d
Unknown sample interacting with An external tip having known radius attached to the end of the lever
Unknown sample absorbed on lever surfaces

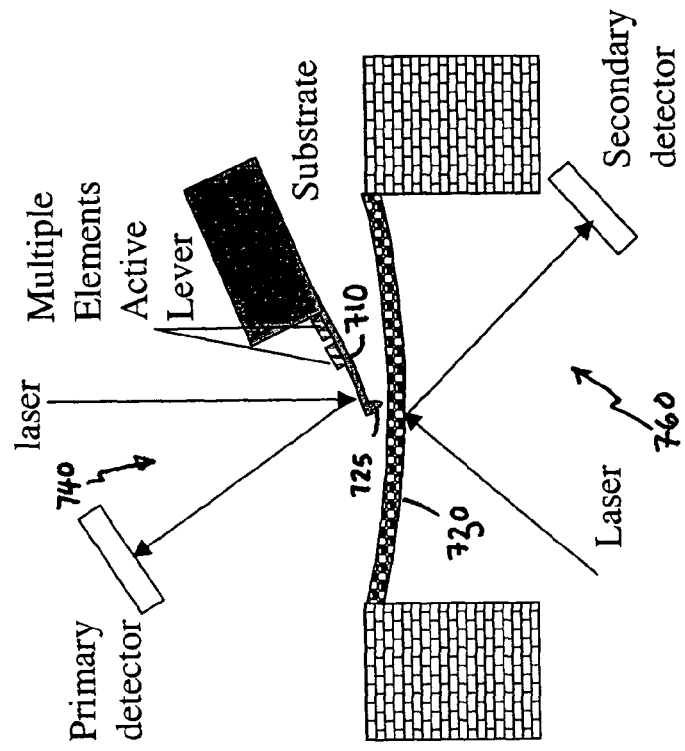
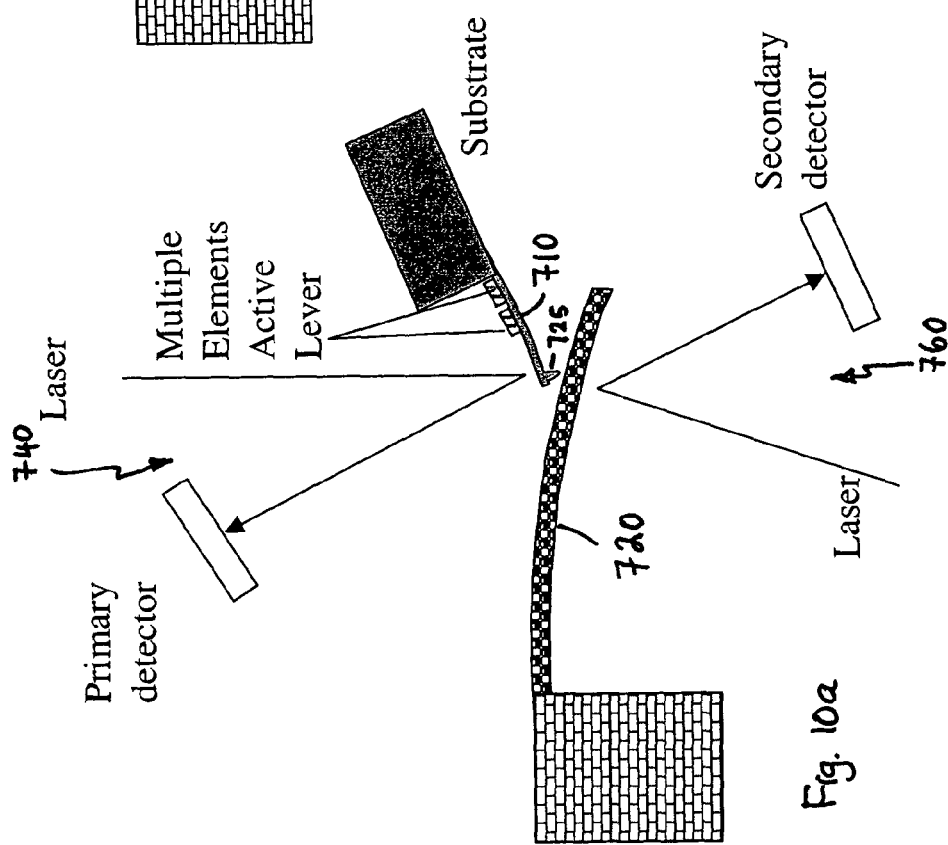
Fig. 10b
Fig. 10a

SYSTEM FOR WIDE FREQUENCY DYNAMIC NANOMECHANICAL ANALYSIS

FIELD OF THE INVENTION

The present invention relates generally to the field of determination of the dynamic mechanical properties of materials. More particularly, the present invention relates to a system that utilizes forces applied at frequencies that are swept over a wide frequency range that includes frequencies higher than the fundamental resonance frequencies of conventional nanomechanical analysis systems in order to perform localized dynamic nanomechanical analysis of small samples, films and surfaces.

BACKGROUND OF THE INVENTION

The quantities determining mechanical response of materials or objects to external force are generally referred as elastic constants. Measurements of elastic response can be performed statically and dynamically. In static measurement the deformation of material at the instance of application of external force indicates compliance of the materials. The amount of deformation is determined by elastic modulus that is a fundamental property of the material. Dynamic measurements, on the other hand, reflect the deformation that changes as a function of time for a constant applied force or frequency dependence of the deformation to external forces. Dynamic measurements produce a complex elastic modulus that changes as a function of frequency of the applied force. The real part of the complex modulus represents instantaneous response of the materials to external frequencies; the imaginary part, which is also frequency dependent, reflect viscous or anelastic response of the materials. For many materials, in particular polymers and biologic materials, the imaginary part of the complex modulus plays a dominant role in determining mechanical response of the material. Dynamic mechanical measurements, therefore, play an essential role for these families of materials.

The procedures and techniques to measure dynamic mechanical qualities of a large sample in response to a given force are well known. For example, the process for determining how a given material responds to an applied stress generally involves placing each end of a relatively large sample that is centimeters long and at least millimeters in diameter into a chuck or clamping device having sensors that can measure the amount of deformation of the sample and the forces applied to the same sample. The sensors can determine the dynamic response of the sample in response to a change in temperature or a change in magnitude and frequency of a tensile or compressive force applied to the sample. Examples of such large-scale dynamic mechanical analyzers are shown in U.S. Pat. Nos. 4,295,374, 4,418,573, 4,506,547, 5,139,079, 5,710,426 and 6,146,013.

While large-scale dynamic mechanical analysis is useful in many contexts, it suffers from a fundamental limitation due to the relatively large size required for the sample. Because the measurements of the dynamic response include contributions from the entire sample, it is not possible to isolate localized variations due to complicated fine structures or defects within a larger structure. Large-scale dynamic mechanical analysis also cannot be applied to micro and nanometer size samples or to thin films because the techniques do not work with relatively smaller sized samples. Furthermore, conventional dynamic mechanical analysis systems are subject to an upper frequency limit in the form of fundamental resonance frequency that is only a few hundred hertz due to the design volume required by such systems in order to cope with large samples. Dynamic mechanical measurements are generally performed below the initial resonant frequency of the measurement system. Because almost all large sized measurement systems have a resonance frequency of only a few hundred hertz, the effective limit on the frequency range is below 200 hz, even in well-refined systems. Dynamic mechanical measurements of materials above a kilohertz are not possible with existing measurement systems.

As a result, research has been devoted to developing instruments and techniques that are capable of performing dynamic nanomechanical analysis on samples in the micron range and smaller, and on thin films. Most of these instruments use a scanning probe microscope or atomic force microscope (AFM) as the basic instrumentation platform. The AFM has an extremely small stylus with a probe tip measuring only nanometers radius that is scanned back and forth across a sample. AFM based measurements have removed some of the constraints of large sample size for mechanical analysis and have made it possible to probe local mechanical properties. A sensor arrangement detects the movement of the stylus relative to the surface of the sample and various calculations and other measurements are used to deduce features of the sample. Examples of current instruments and techniques for performing dynamic nanomechanical analysis are shown in U.S. Pat. Nos. 5,329,808, 5,700,953, 5,764,068, 5,675,075, 5,866,807, 6, 006,593, 6,095,679, 6,185,991, 6,349,591 and 6,200,022. All of the existing arts described in these patents use a piezo actuator to shake the sample or to shake the base of the cantilever as the tip of the cantilever is in contact with the sample.

The basic parameters acquired in the dynamic mechanical analysis are real and imaginary part of the modulus. The ratio of these two parameters determines the quality factor of the material, which is also interpreted and measured as phase lag between the applied stress and the responding strain of the sample. Frequency dependence of this phase lag has become the signature of viscoelasticity or anelasticity of the polymeric, biological or metallic materials. A paramount issue in dynamic mechanical analysis (DMA) instrument design is to eliminate any system mechanical resonance so that the phase lag detected does not contain any contribution of the resonance induced phase shift.

A review of the mathematical theory for measuring dynamic mechanical responses highlights the apparent reasons for this fundamental limitation. In order to determine an elastic response of a material, for example, a periodic force is applied to the sample. The elastic part of the deformation of the sample exhibits its resistance to the periodic force as the real number part of the modulus of elasticity ($E_{real}$). The anelastic or viscoelastic deformation of the sample in response to the periodic force appears as the imaginary part of modulus of elasticity ($E_{imaginary}$). The phase lag $\phi$ measured between the applied stress represented by the periodic force and the sample response is an intrinsic material property called internal friction ($Q^{-1}$), which is expressed as:

$$Q^{-1} = E_{imaginary}/E_{real} \tag{1}$$

If the periodic force is applied to the sample at a frequency far below any resonant frequency or frequencies of the measurement equipment, then the internal friction ($Q^{-1}$) is related to the phase lag $\phi$ between applied stress and sample deformation as:

$$Q^{-1} = \tan \phi \tag{2}$$

In mechanical measurement systems where the system exhibits a resonance, the phase lag θ between the applied stress and the measured deformation response can be induced by both the material property of the sample and the resonance of the measurement system. The relationship for this is shown in the following equation:

$$\tan\theta = \omega_r^2 * Q^{-1}/(\omega_r^2 - \omega^2) \quad (3)$$

where, $\omega_r$ represents the resonance frequency of the measurement system and ω is the measurement force frequency of the applied stress. It can seen from Eq. (3) that only when the measurement force frequency ω is far away from the resonance frequency of the measurement system can the phase lag θ between the applied stress and the measured response be correlated to the intrinsic material property $Q^{-1}$, or $\tan\theta = Q^{-1}$ when $\omega \ll \omega_r$. Around the resonance point, the term $1/(\omega_r^2 - \omega^2)$ dominates the phase between the applied stress (in the form of the reference signal from a spectra analyzer) and the measured response (in the form of a signal from the AFM), giving a 180-degree phase shift. Because the phase shift due to resonance substantially overrides any phase lag due to the intrinsic material property, the phase lag θ no longer correlates directly to mechanical properties of the sample materials, but rather is dominated by the resonance of the measurement system.

In the context of the mechanical spectra, the real part elastic modulus ($E_r$) and imaginary part elastic modulus ($E_i$) of a material can be generally expressed as:

$$E_r(\omega) = E_r + \Sigma \delta E_i^*(\omega\tau_j)^2/(1+(\omega\tau_j)^2) \quad (4)$$

and $$E_i(\omega) = \Sigma \delta E_i^*(\omega\tau_j)/(1+(\omega\tau_j)^2) \quad (5)$$

where, $E_r(\omega)$ and $E_i(\omega)$ are the mechanical spectra of a viscoelastic or anelastic material, exhibiting the dependency of real and imaginary parts of the modulus of the material as a function of frequency. The summing with subscript j represents contribution of independent microscopic mechanisms to the total spectra. This frequency dependency can be measured as function of the phase lag ϕ according to Eq. 2. Again, Eq. (3), with respect to the phase lag θ, indicates that these measurements should be made only at frequencies far away from any mechanical resonance of the measurement system.

As a result, all of the commercially available systems capable of performing dynamical mechanical analysis (DMA) operate only at frequencies below 200 Hz because the measurement system resonance can start as low as a few hundred hertz and becomes significantly worse at higher frequencies. In the context of dynamic nanomechanical analysis using an AFM, the complications of resonance frequency of the measurement system can be even more severe due to the more complicated nature of the measurement systems. U.S. Pat. No. 5,700,953 describes the use of a small sinusoidal force imposed on the sample by a piezoelectric element that controls the distance between the tip and the sample in an effort to deal with the problems of resonance. U.S. Pat. No. 6,200,022 describes the use of small constant frequency variations in the temperature of the probe and sample that are used to create a thermal stress applied to the sample to deal with the problem of resonance in a thermal context.

In other uses of an AFM, it is common to vibrate the mounts of the probe tip against the sample at a constant frequency in order to produce intermittent contact with the sample as part of the surface measurement. This technique, known as a Tapping-Mode® AFM, was pioneered by the assignee of the present invention and is described, for example, in U.S. Pat. Nos. 5,412,980, 5,519,212 and 6,008,489. Unlike the use of an AFM for dynamic nanomechanical analysis, however, the intermittent contact mode is intentionally operated at the resonance frequency of the AFM. For example, U.S. Pat. Nos. 5,902,928 and 6,318,159, describe how to compensate for the problem of varying resonance frequency that changes as the probe tip is advanced toward a sample.

In U.S. Pat. No. 5,866,807, a two-stage approach is used to avoid the problem of resonance in measuring the dynamic mechanical deformation properties of a material using an AFM. In the technique taught by this patent, a permanent indentation is made in the material during an initial pass. The depth and the feature characteristics of that indention are then measured during a subsequent pass where the AFM is operated at the resonance frequency. While this technique offers less information because it does not apply a force signal at higher frequencies, it does avoid the problem of resonance of the AFM as a measurement system.

U.S. Pat. No. Re. 36,488 describes an embodiment of the operation of an AFM in an intermittent contact mode where changes in which the phase and frequency response of the cantilever probe over a narrow range of frequency modulations centered about the resonance frequency are measured in order to determine the degree of damping induced on the cantilever probe by the sample. While some useful information can be discerned from these measurements, again the focus of using the AFM as a measurement instrument is on operation at or near the resonance frequency. The AFM system described in this patent is not able to provide material properties in a wide range of continuous frequencies.

U.S. Pat. No. 6,318,159 describes a scanning force microscope that operates in an approach mode as a vibrating probe tip is driven into proximity with a surface of a sample to be examined, and in a scanning mode as the vibrating probe tip is moved along the surface to measure its characteristics. In the approach mode, the frequency of tip vibration is preferably varied to maintain a constant phase angle between the motion of the probe tip and the motion of the actuator driving the probe tip in vibration through a cantilever. Operation in the scanning mode follows operation in the approach mode, with vibration of the probe tip in the scanning mode being at the last frequency used in the approach mode. This patent also discloses a method for automatic engagement of the tip of a scanning force microscope, in an AC detection mode, with the probe tip being vibrated at or near its resonant frequency by an excitation voltage signal applied to the excitation segment. One component of this method modulates the tip to surface distance in order to facilitate the measurement of a value of the slope (dA/dZ) of the curve of vibration amplitude (A) as a function of the tip-to-surface separation, a value which is used as a parameter for stopping the process of increasing the engagement of the tip to the sample surface. A second component of this method uses a phase-frequency servo algorithm to monitor the shift in resonance frequency and, accordingly, to adjust the driving frequency in real time, keeping the driving frequency in a desired region of operation at all times, somewhat like a dithering signal that corrects for drive frequency in response to cantilever resonance frequency as the tip is interacting with the surface of the sample in a 'non-contact' mode. While this patent discloses several approaches for controlling the frequency of operation, it will be noted that the cantilever in this system is operating only at its resonance frequency.

The most used method to derive material properties on AFM platform is so called force modulation measurement. In this technique, the probe tip is brought into constant contact with sample surfaces. An AFM feedback loop using the cantilever deflection as feedback parameter is employed to maintain a constant contact force between the tip and the surfaces. A piezo element mounted on the sample holder or the tip holder is used to modulate the sample or cantilever at a fixed frequency. The phase or amplitude of the cantilever motion thus determined is then correlated to material mechanical properties. This force modulation technique can be found in a rich collection of published works or patents. However, all of the existing techniques share the same problem, i.e., the drive force used to modulate the sample or the cantilever is tens of thousands to hundreds of thousands times more than what is needed to deform the cantilever at the desired frequency. Such substantially overpowered drive creates numerous parasitic resonances, rendering wide frequency mechanical spectra measurement impossible. All the reported measurements or patents are either restricted in a single modulation frequency or a very narrow frequency range. Wide, continuous frequency range dynamic mechanical analysis of mesoscale to nanometer scale remains a challenge.

Additional problems encountered in dynamic nanomechanical analysis are the limitations imposed by the actuating materials and the mechanical bandwidth of the mechanical assembly. The bi-layer actuation generated by the piezo stack actuator, for example, currently has a mechanical bandwidth of up to 50 kHz. due to the resonance of the active layer. The piezo stack actuator also has residual or parasitic resonances spread all over the frequency range, even though the individual plates can have resonances above the MHz range.

It would be desirable to provide for a system capable of performing dynamic nanomechanical analysis over a broad range of frequencies that can overcome the limitations of existing DMA systems and that includes frequencies higher than the resonance frequency of those DMA systems.

SUMMARY OF THE INVENTION

The present invention provides methods and apparatus for performing dynamic nanomechanical analysis of a sample using a cantilever probe that interacts with the sample using a force applied across a wide range of frequencies that includes frequencies greater than 300 Hz. The motion of the cantilever probe is detected in response to the applied force over the range of frequencies and analyzed over at least a portion of the wide range of frequencies to determine dynamic mechanical properties of the sample. The analysis of the motion of the cantilever probe is preferably performed in terms of amplitude, phase, and frequency of both the probe and the sample and, preferably, where the applied force is analyzed to determine both a real and an imaginary modulus of a mechanical response of the sample. Preferably, the force is applied so as to produce a minimum of phase response variation in the absence of the sample.

The key concept of the present invention is to localize the applied modulation force so that the force is only applied to the cantilever and therefore remove all the interference from the parasitic resonances of the existing arts. By doing so, the phase lag between the applied stress and the response can be directly correlated to mechanical Q of the material in a wide and continuous frequency range. A multiple patterned active element in the present invention also allows applying forces in different directions concurrently or intermittently so that the sample interaction with the probe tip can be analyzed in more than one dimension of interactions.

In a preferred embodiment, the present invention applies a high frequency signal (in the range of hundreds of megahertz) to a single micron size wire positioned about the cantilever probe. The high frequency signal in the microwire causes electromagnetic interaction between the wire and the nearby cantilever probe. Such drive force also restrains the applied force to the cantilever only. As a result of this arrangement, the effective fundamental resonance of the nanomechanical analysis system in accordance with the present invention is pushed into the Megahertz range. Consequently, the operative frequency range for the preferred embodiment can be from sub-hertz to a few Megahertz and works in both air and fluidic environments.

The present invention overcomes the problems of parasitic resonance in the measurement system by minimizing the amount of resonance that is introduced into the system in order to accomplish the necessary measurement. In order to achieve sensitivity down to a mono molecule layer, a micro cantilever probe is used because only a micro cantilever probe has such a sensitivity. Given that the micro cantilever probe has a perfect mechanical boundary at the joint with the cantilever substrate (the fixed end of the cantilever, the probe end is fabricated through wet/dry etching and is eventually relieved as an extension of the same material in a diving board shape), the parasitic resonances observed in force modulation or direct drive of the cantilever are most likely due to the applied force which drives the cantilever substrate or holder or the sample holder into oscillation. In the case of driving the cantilever substrate, a piezoelectric plate is used to drive the cantilever substrate into motion, i.e., the fixed end of the cantilever. As a result, the piezoelectric plate has to drive an object that is more than 10,000 heavier than the cantilever into motion before any force can be transmitted to the micro cantilever. The present invention recognizes that the substantial overdrive of the cantilever substrate is sufficient to cause parasitic resonance of nearby complicated mechanical systems. The over-powered modulation of the sample holder shares the same problem. The key to achieving clean response, as taught by the present invention, lies in using a clean drive force that drives the micro cantilever probe only and directly.

One objective of the present invention is to overcome the parasitic resonance in conventional dynamic nanomechanical analysis systems, which occurs as low as a few hundred hertz, and expands the dynamic nanomechanical measurements into the megahertz range. Another objective is to enable dynamic nanomechanical analysis in small sized samples, such as mono molecular or atomic layer materials on a cantilever probe. Another objective of the invention is to perform localized dynamic nanomechanical measurements so that the sample interaction with the applied stresses is restricted into the region as small as tens of nanometers. Yet another objective is to apply forces of different directions concurrently or intermittently so that the material under study can be examined not only in multiple frequencies but also multiple force components. An advantage of the present invention is that it enables atomic force imaging and localized dynamic nanomechanical measurements to be performed during the same procedure in a single instrument. Another advantage of the present invention is that it enables a determination of mechanical spectra in terms of both shear force and compressive force to be performed in-situ at the same localized location of a sample.

BRIEF DESCRIPTION OF THE DRAWINGS

FIGS. 6a–6d are schematic side views of alternate embodiments of cantilever probe actuation modes.

FIGS. 7a–7d are schematics of different drive configuration where one active lever is used to drive another passive lever FIGS. 8a–8d are schematic side views of alternate embodiments with the sample coated or absorbed on the cantilever in accordance with the present invention.

FIGS. 10a and 10b show the deformable sample platforms with their own deformation detection systems.

FIG. 16a–16c are graphs of simultaneous measurements of the sample topography, response phase and amplitude changes.

DETAILED DESCRIPTION OF THE PREFERRED EMBODIMENTS

The present invention relates generally to the field of determination of the dynamic mechanical properties of materials. More particularly, the present invention relates to a system that utilizes forces applied at frequencies that are swept over a wide frequency range that includes frequencies higher than a resonance frequency of the system in order to perform localized dynamic nanomechanical analysis of small samples, films and surfaces.

Figure 1:
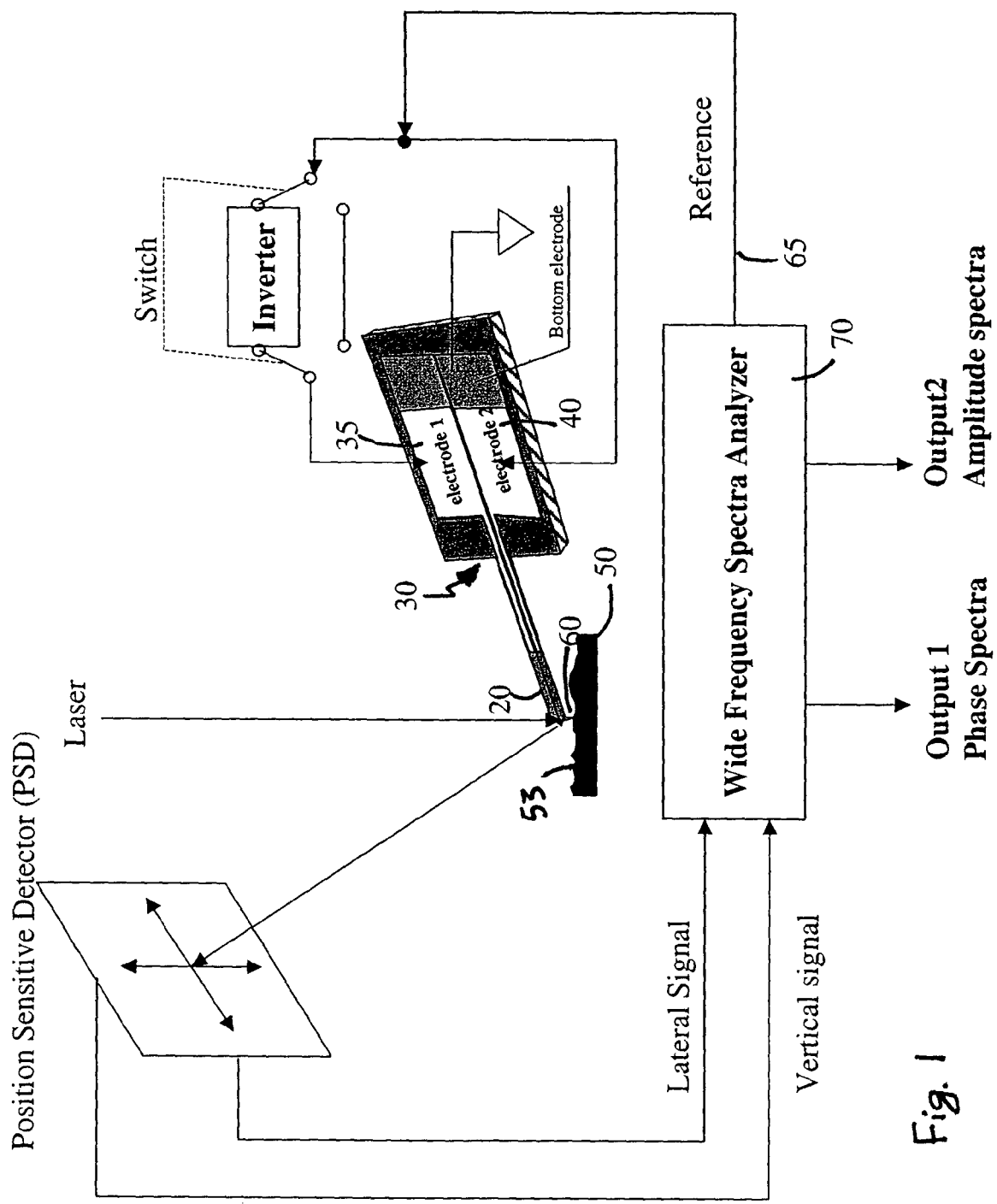
FIG. 1 is a schematic showing the principle of operation of a preferred embodiment of the present invention.

FIG. 1 is a schematic showing the principle of operation of a preferred embodiment of the present invention. A cantilever 20 with active elements 30, such as, for example, a piezo electric layer sandwiched between top 35 and bottom 40 electrodes is used to drive the front part of the lever 20, interacting with the sample 50 at the tip 60 which is in contact with the sample 50. The top electrodes 35 are electrically separated into two areas. A periodic signal 65 from a spectra analyzer 70 is applied to top electrodes 35 and 40 either in phase or out of phase. When signal to electrodes 35 and 40 is out of phase, the cantilever 20 is forced to perform rotational motion, causing friction between tip 60 and sample 50 below. The spectra analyzer 70 would then sweep frequency continuously from 1 Hz to 10 Mhz (or below), the phase and amplitude response as a function of frequency yields data of viscoelastic and anelastic properties of materials such as, for example, the sample 50, immediately under the tip 60. When sample 50 is pushed against the tip 60 with a different force, the phase and amplitude spectra of the materials, such as the sample 50, is then measured under different vertical loads. In this case, the measurements yield visco and anelastic properties under different compressive stresses.

Figure 2:
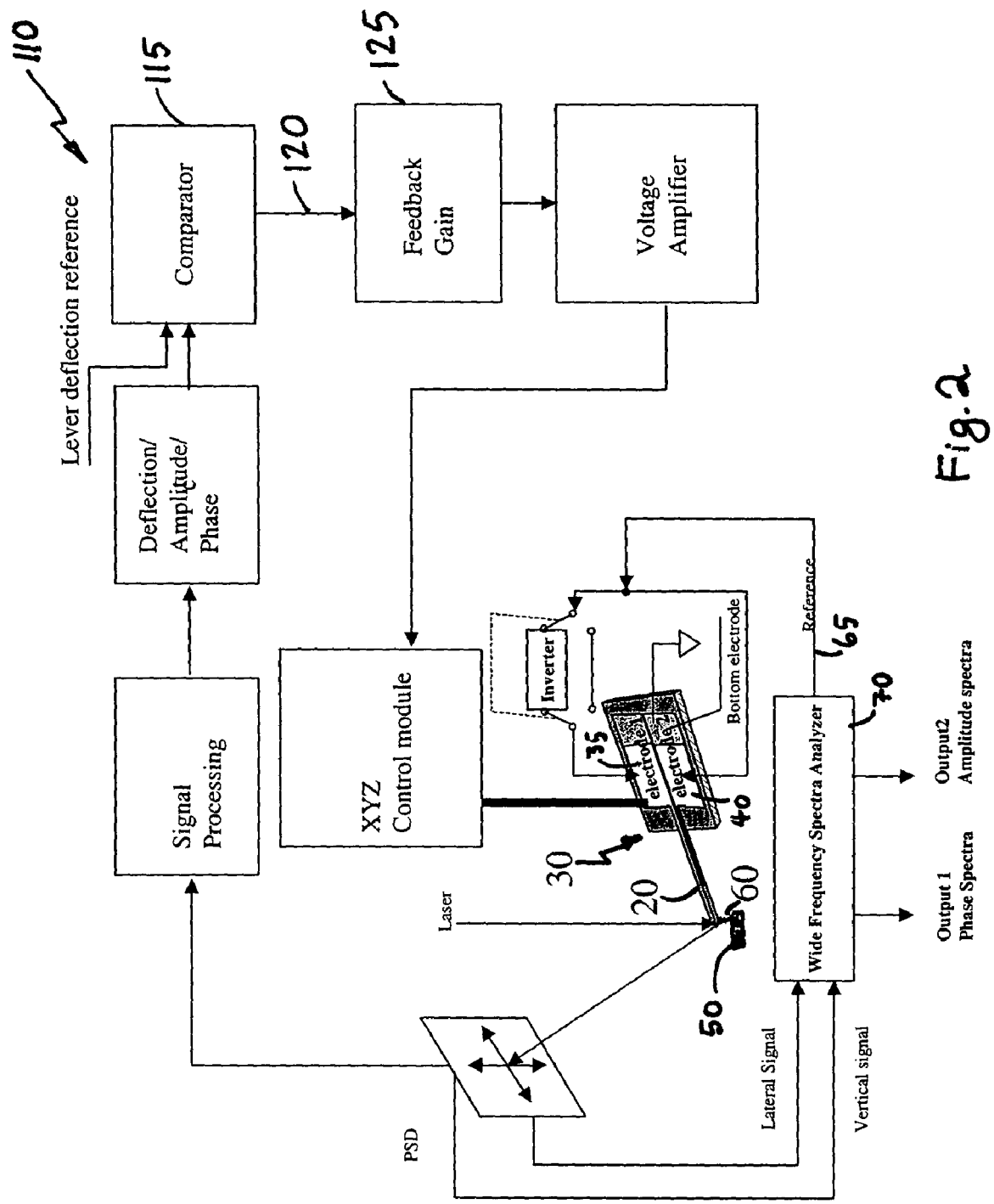
FIG. 2 shows another embodiment of the present invention wherein the mechanical spectra measurement is coupled to a position and force feedback control system.

FIG. 2 shows another embodiment of the present invention. Here the mechanical spectra measurement is coupled to a position control and interaction force feedback system 110 such as the one used in atomic force microscopy. The vertical cantilever deflection of the cantilever 20 represents preload for the force between tip 60 and sample 50. It is compared to a preset number at the comparator 115 and produces an error signal. The error signal 120 is then multiplied by a feedback gain 125, which is normally P(proportion)/I(integral) gain and further amplified to drive the Z component of the XYZ position actuators. The coordination of the feedback loop reduces error towards zero, rendering the tip 60 in a predetermined contact force or proximity contact on sample 50. The art of the AFM feedback control to maintain constant contact force is well known in the prior art. Simultaneously, an alternating signal is applied to electrodes 35 and 40 of the microactuator 30 to modulate cantilever motion as shown in FIG. 1. The phase spectra and amplitude spectra are acquired at a position on the sample surface 53. The xyz controller 30 is then ready to move the tip 60 to the next position in xy plane to perform the same measurement under the same conditions. The advantage of the combined system is two fold: Firstly, it eliminates thermal and mechanical drift of the tip holder (not shown) relative to sample holder (not shown). Secondly, it allows AFM imaging and spectra measurements to be obtained simultaneously, providing both topological and mechanical property information of the samples. In a particularly interesting area of the sample, a full spectral range from 1 Hz to 10 Mhz could be measured in a matters of seconds.

Figure 3:
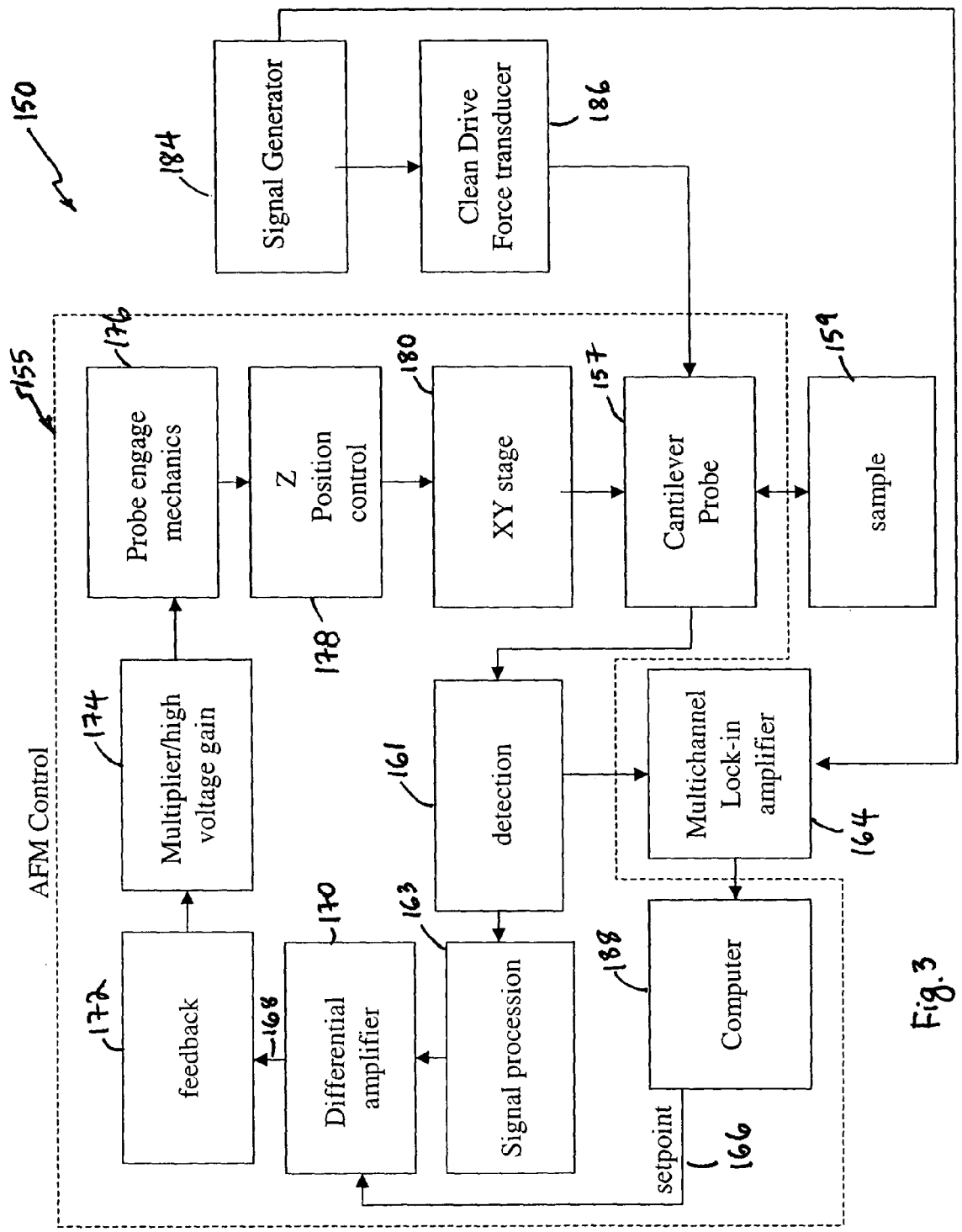
FIG. 3 shows a block diagram of a preferred embodiment.

FIG. 3 shows a block diagram 150 of the preferred embodiment. Inside the dotted line box 155, a conventional atomic force microscope and its control system is schematically displayed. Such a system is well known in the art listed in the background section. In the prior art, an engagement system brings the cantilever probe 157 to interact with the sample 159. The magnitude of interaction is determined by the cantilever deflection in its DC or AC motion. Such motion is detected through optical means or other displacement transducers 161 and then goes through a signal processing element 163. Signal processing includes filtration, RMS-DC conversion, or lock-in amplifier 164. The output of the signal processing element 163 is then compared with a preset value 166 which defines strength of the interaction, yielding error signal 168 through the differential amplifier 170. The error signal 168 goes further through feedback control element 172, normally with, but not limited to, proportion and integral gains. The output of the feedback control element 172 is further modified by a high voltage gain and/or multiplier 174 and sent to positioning elements 176, Z position control piezo in particular 178, to move the cantilever 157 up or down in order to minimize error signal 168. Upon completion of the error control, the xy stage 180 or piezo will move the cantilever probe 157 to the next position to interact with the sample 159 again. Raster scanning of the sample yields topographic image or other interaction properties. In the present art at each location of tip-sample interaction, a composed signal with various frequency components from signal generator 184 is sent to a clean drive system 186, defined in the next two figures, FIGS. 4 and 5. Such a drive force will perturb the tip/sample interaction in a wide frequency range. The components of the composed signal are also sent to the multichannel lock-in amplifier 164 with one or more signal channels serving as references. The detected response due to the perturbation is then passed to the multichannel lock-in 164, producing phases and amplitudes output to the computer 188. If the composed signal is only a single frequency sinusoidal signal, the wide frequency sweep is obtained by varying frequency of the signal generator 184 while the AFM control system 155 maintains tip/surface interaction constant, normally through a preloaded contact force. If the composed signal from the signal generator 184 contains multiple frequency components, the sweep can be acquired simultaneously for all the said components.

Figure 4:
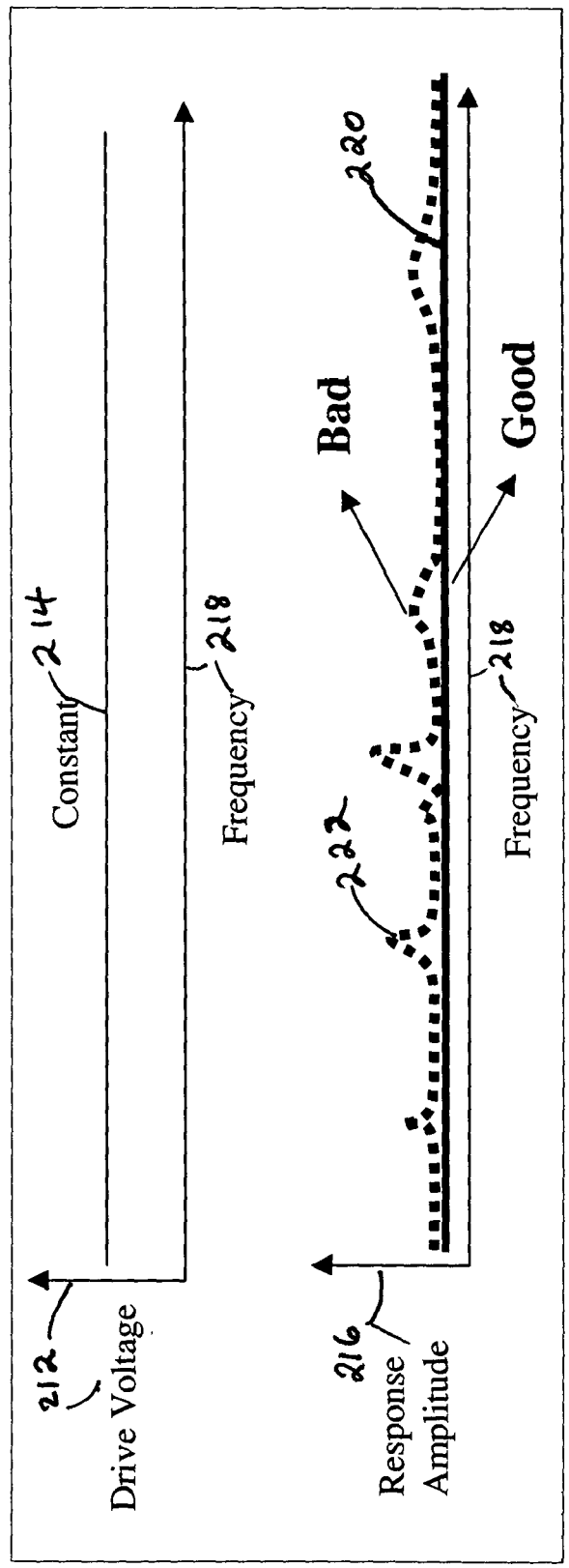
FIG. 4 explains a test based on the response of amplitude that qualifies the applied force, which is free of resonance and can be used for the dynamic mechanical measurements.

FIG. 4 represents a test 210 that qualifies the force used to perform dynamic mechanical spectra analysis through the amplitude. The upper part shows the applied force in terms of voltage 212 for piezo electric actuators, the leveled straight line represents a constant actuation amplitude 214. The lower part shows the response amplitude 216 of a dummy sample which has no frequency characteristic. Such a sample can be a single crystal of silicon free of defects at room temperature. As frequency 218 sweeps in the range of measurements, the response should remain constant throughout the entire spectra, as shown in the solid line 220 in the lower figure. The dotted line 222 in the lower figure represents a drive that is not qualified for such mechanical spectra measurements because of its variation.

Figure 5:
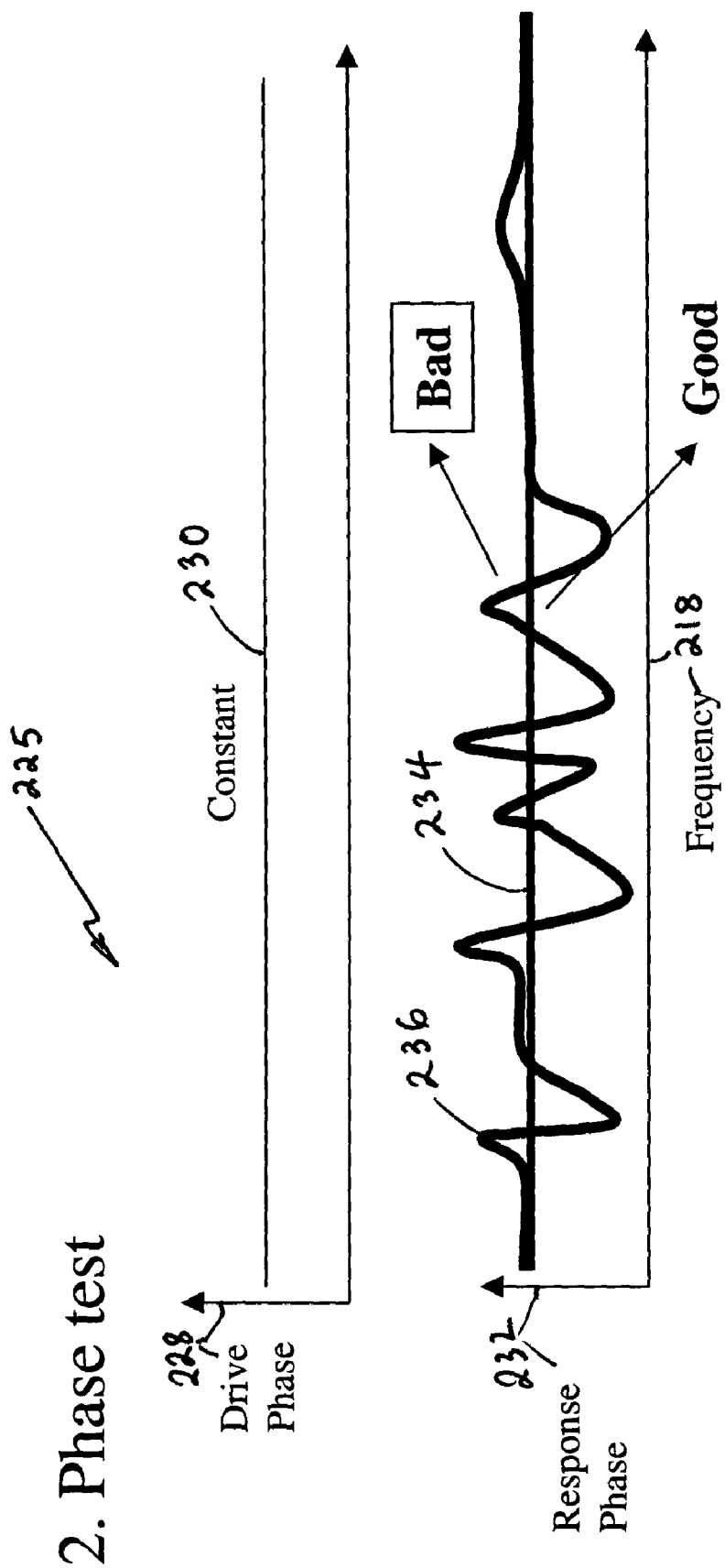
FIG. 5 explains a test based on the response of phase that qualifies the applied force, which is free of resonance and can be used for the dynamic mechanical measurements.

FIG. 5 represents a test 225 that qualifies the force used to perform dynamic mechanical spectra analysis through the phase 228. The upper part shows the applied force in terms of phase for piezo electric actuator drive, the leveled straight line 230 represents a constant actuation phase. The lower part shows the response phase 232 of a dummy sample which has no frequency characteristic. Such a sample can be a single crystal of silicon free of defects at room temperature. As frequency 218 sweeps in the range of measurements, the response phase 232 remains constant throughout the entire spectra, as shown in the solid line 234 in the lower figure. The dotted line 236 in the lower figure represents a drive that is not qualified for such mechanical spectra measurements because of its variation.

FIGS. 6a–6d are schematic side views of alternate embodiments of cantilever probe actuation modes. The forces can be generated in a variety of ways as shown in FIGS. 6a–6d. For example, the actuation force may be provided by means of a micropiezo composite lever drive 300, as shown in FIG. 6a. The micropiezo drive 300 comprises a piezo layer 310 sandwiched in between two metal films, top layer 320 and bottom layer 330, which also serve as the electrodes. The bimorph actuation, representing clean piezo drive, currently has a bandwidth of up to 50 k–100 kHz, due to the resonance of the active lever. In contrast to previous art where piezo elements are mounted on the sample holder or cantilever holder, the composite active lever shows a clean spectra in the range up to 50 khz that satisfy the tests presented in FIGS. 4 and 5. FIG. 6b exemplifies another embodiment of the present invention comprising a device 350 having a wire-shaped actuation device 355 positioned above the cantilever 20. The wire 355 drives the cantilever 20 at high frequency (100–300 Mega Hertz) due to induced electromagnetic interaction, without exciting any other part of the structure. FIG. 6c exemplifies an alternative embodiment of the invention. The actuation device is a capacitive drive 380 essentially comprising a capacitor plate 385 positioned above the cantilever 20, and driving the cantilever 20 at low frequency (1 Hz–1 Mhertz) due to the electrostatic interaction force. An alternate embodiment of the actuation device 390, depicted in FIG. 6d, consists of an ultrasonic drive 395 which drives the cantilever 20 at a frequency of 10 to 500 MHz, due to ultrasonic pressure. In each of the force transducers mentioned above, the forces are applied locally and directly to the microlever or cantilever 20. There is no mechanical excitation of the cantilever holder (not shown) or external mechanical system (not shown) thereby rendering an extremely clean drive force so that there are no parasitic resonances of the external mechanical system involved.

In FIGS. 7a–7d, alternative embodiments of a drive with an active cantilever to deform another passive lever are illustrated. In FIG. 7a, the passive lever 410 is a natural extension of the active lever 420. On the active lever 420, multiple piezo elements 425 are patterned so they can deform the underlying lever material through coordinately applied signals to each individual element. For instance, if the upper two elements 427 and lower two elements 429 have out of phase voltage signals, the coordinated drive voltages will deform the active lever 420 torsionally. However, if the left pair and right pair have opposite phase signals, the coordinated drive voltage will rock the lever 420 flexurally. The amplitude of voltage applied to each element can be varied independently so that the asymmetry, due to imperfection of the lever production, can be balanced or compensated. Similar drive can be applied to the configuration exemplified in FIG. 7b where the active elements 425 are piezo plates operating independently, providing torsional, flexural drive with possibility of balance compensation through individual element. In this case, only a passive lever is needed. In FIG. 7c, the multiple elements, active lever 430, is used to deform a passive lever 432 through direct mechanical contact. All of the possible drive mechanisms available in FIG. 7a can be applied to the passive lever by contact mechanical load transfer. FIG. 7d is a situation similar to the situation of FIG. 7b, except that the passive lever 434 is an independent mechanical part and the load transfer, the passive lever has to be through mechanical contact.

Alternate embodiments of the device 500 of the present invention is exemplified in FIGS. 8a–8d. FIG. 8a shows a sample 510 in the form of a coated layer on the microcantilever 20. In free oscillating levers, the goal is to determine viscoelastic properties of a coating or absorption on a known cantilever. The governing equation for a freely oscillating cantilever with a coating of thickness D is given by:

$$Q_{total}^{-1} = Q_{lever}^{-1} + 3 * \frac{E_{coating} D_{coating}}{E_{lever} D_{lever}} * Q_{coating}^{-1} \qquad (6)$$

where $Q^{-1}$ is defined as in equations 1, 2 and 3 above, but refers to different part of the materials. In the lever/coating composite, D represents the thickness and E the Elastic Modulus. Subscripts refer to the relevant quantities of either the lever or the coating. Since $Q^{-1}{}_{lever}$ is usually a few orders of magnitude lower than $Q^{-1}{}_{coating}$, the measurement parameter $Q_{total}$ is diluted by the thickness ratio. Bohn and Su, *Mat. Res. Symp. Proc.* Vol 239, p215. The cantilever 20 should be driven at a frequency below its resonance frequency in order that the phase directly relates to the imaginary part of the modulus ($E_{imaginary}$), as defined in Eq. 1 above. On the other hand, when the cantilever is driven at its resonance the imaginary part of modulus can be derived form free decay of the resonance amplitude after the actuation force is removed.

In another embodiment illustrated in FIG. 8*b*, the sample 520 is in the form of an absorbed layer on the microcantilever 20. The relationship between the measured phase as a function of frequencies of the drive forces is similarly defined through equations 1–6 above, except that the thickness of the absorption layer may not be well defined. Each of FIGS. 8*c* and 8*d*, depict an embodiment wherein the sample 50 is located separately from the microcantilever 20 and a tip 60 is interacting with the surface 53 of the sample 50. The tip is physically attached to the cantilever 20. The tip 60 can be one of several embodiments. In one embodiment illustrated in FIG. 8*c*, the tip 60 is shaped like a stylus with the radius of the tip ranging from a few nanometers to infinity (meaning a flat bottomed tip). A very consistent and distinctive problem related to the quantitative mechanical measurements using tip/sample contact interaction is the unknown contact area and inhomogeneous load on the sample from the sharp tip. In another embodiment shown in FIG. 8*d*, the tip 62 is a ball shape 525 with known radius externally attached to a tipless cantilever. In this case, the contact area of the tip with the sample surface 53, can be controlled and the contact area (not shown) quantitatively known. The blunt tip such as, for example, the ball tip described above, is supposed to be shaped with a known radius of curvature such that the load is applied homogeneously and the contact area can be derived from the depth of the deformation.

Figure 9A:
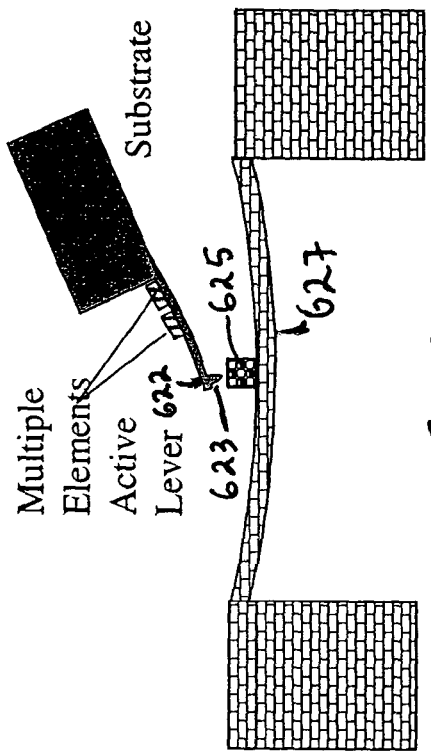
FIGS. 9a–9d represent different sample configuration for samples on a deformable platform.
Figure 9B:
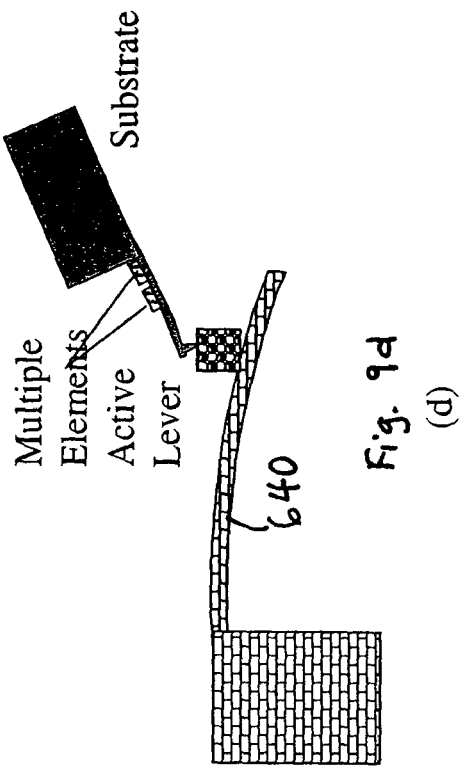
Figure 9C:
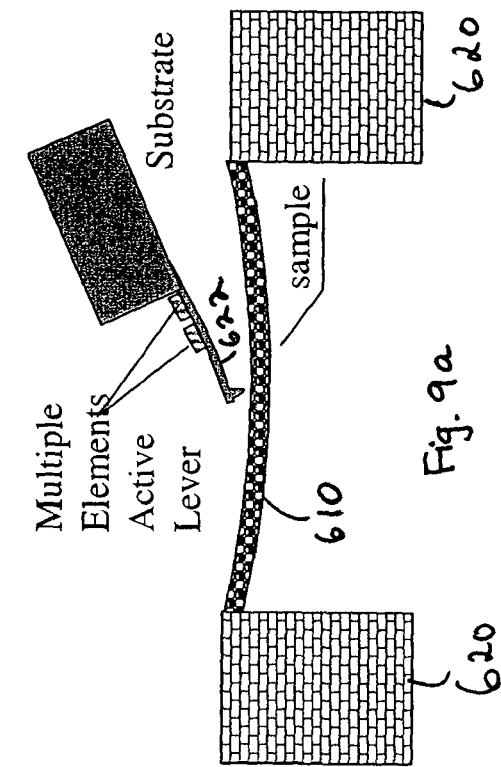
Figure 9D:
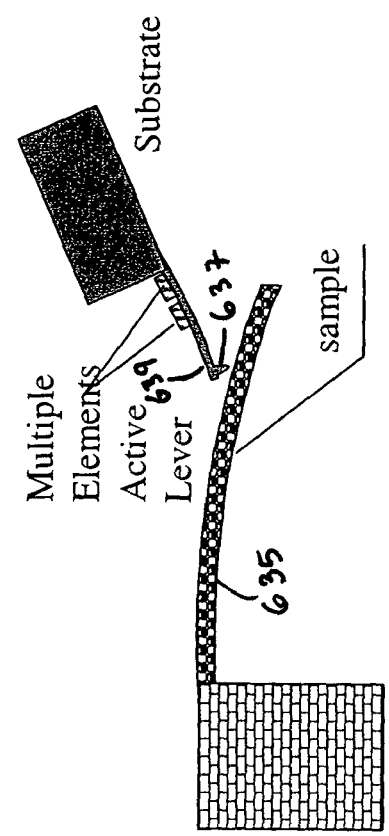

FIGS. 9*a*–9*d* further illustrate alternative embodiments of samples with well-defined boundary constraints being deformed by a clean spectra active lever. In FIG. 9*a*, the sample 610 consists of a material whose properties are to be determined, in the shape of a bridge or a membrane with the peripheral fixed on the substrates 620. An active lever 622 is then used to deform the membrane or bridge-shaped sample and perform wide frequency mechanical spectra analysis. FIG. 9*b* represents another embodiment of sample where a nanometer to micrometer sized sample 625 is placed on a deformable base 627 with well-defined mechanical boundary constraints, such as membrane or bridge. The active lever 622 applies load to the sample 625 through the tip 623 and the applied force can be directly assessed by the deformation of the deformable sample base 627. Yet another embodiment is shown in FIG. 9*c* with a configuration that is similar to that depicted in FIG. 9*a*, except that the deformable sample 635 is in the shape of a lever, deformed passively through load transfer at the contact point 637 of the active cantilever probe 639. FIG. 9*d* shows a situation similar to the situation in FIG. 9*b*, except that the deformable base 640 is a cantilever with known mechanical properties.

FIGS. 10*a* and 10*b* represent alternative embodiments of the detection systems where the active lever element 710 and the passive lever 720 each has its own detection system to determine deformation. The advantage of such arrangements with the secondary detection system is that the force imposed by the tip contact of the active lever 710 can be determined independently. In FIG. 10*a*, the upper lever 710 assumes an active role and generates forces of wide frequency to deform the sample lever 720 by the tip contact 725. The deformation can be directly measured by the secondary detection system 760. A well established and calibrated force and deformation relationship will lead to quantitative determination of real modulus, imaginary modulus, and mechanical quality factor. FIG. 10*b* represents a similar situation as FIG. 10*a* but with a differently constrained sample 730, such as membrane or bridge. Any of the globally deformable samples shown in FIGS. 10*a* and 10*b* can be replaced by sample shapes or combinations of any choice in FIGS. 9*a*–9*d*.

Figure 11:
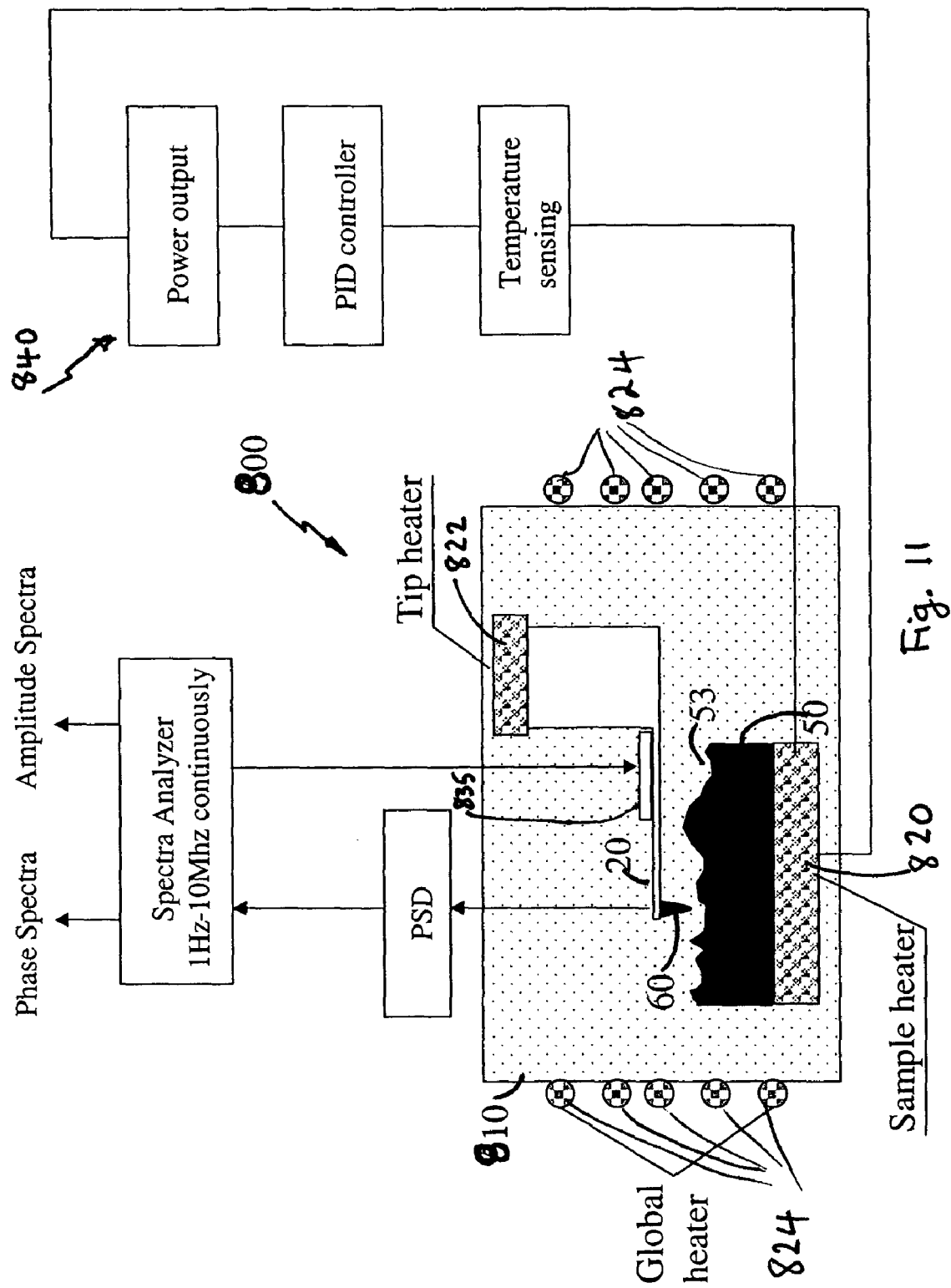
FIG. 11 is a schematic of an alternate embodiment of the present invention incorporating temperature control.

The embodiment shown in FIG. 11 illustrates a preferred embodiment where the measurement environment such as temperature, gaseous or fluidic media surrounding the sample are controlled and the mechanical spectra measurement performed in combination with these controls. The subsystems 810 can be a closed chamber providing isothermal or controlled gaseous and fluidic environment. The temperature control system 800 is a known art. A temperature sensor (not shown) embedded in the sample accurately measures the temperature of the sample. This temperature measurement is used in a feedback loop 840 of the temperature control system 800 to control the temperature of the sample 50. Although, temperature control and sensing is a well known art, the device in this invention teaches the sample being heated using the tip 60 of the microcantilever 20, which prevents deposition of the sample evaporate onto the cantilever surface. The heaters presented in this embodiment, sample heater 820, tip heater 822 and global heater 824 which heats the entire chamber, can be used individually or in any combination thereof.

In an alternative embodiment 800 of the system of FIG. 11 as described above, the mechanical spectra measurement is again combined with temperature control unit as already exemplified. However, in another preferred configuration, the temperature can be monitored by a secondary cantilever (not shown), which has the same thermal inertia as the sensing cantilever 20 but without the active coating layer 835. For a simple Si microcantilever the frequency varies linearly with the temperature change and serves as a good indication of the temperature. This configuration is particularly useful if the material of the sample 50, whose temperature is to be measured, is coated on the sensing cantilever 20, as shown in FIGS. 8*a* and 8*b*.

Figure 12:
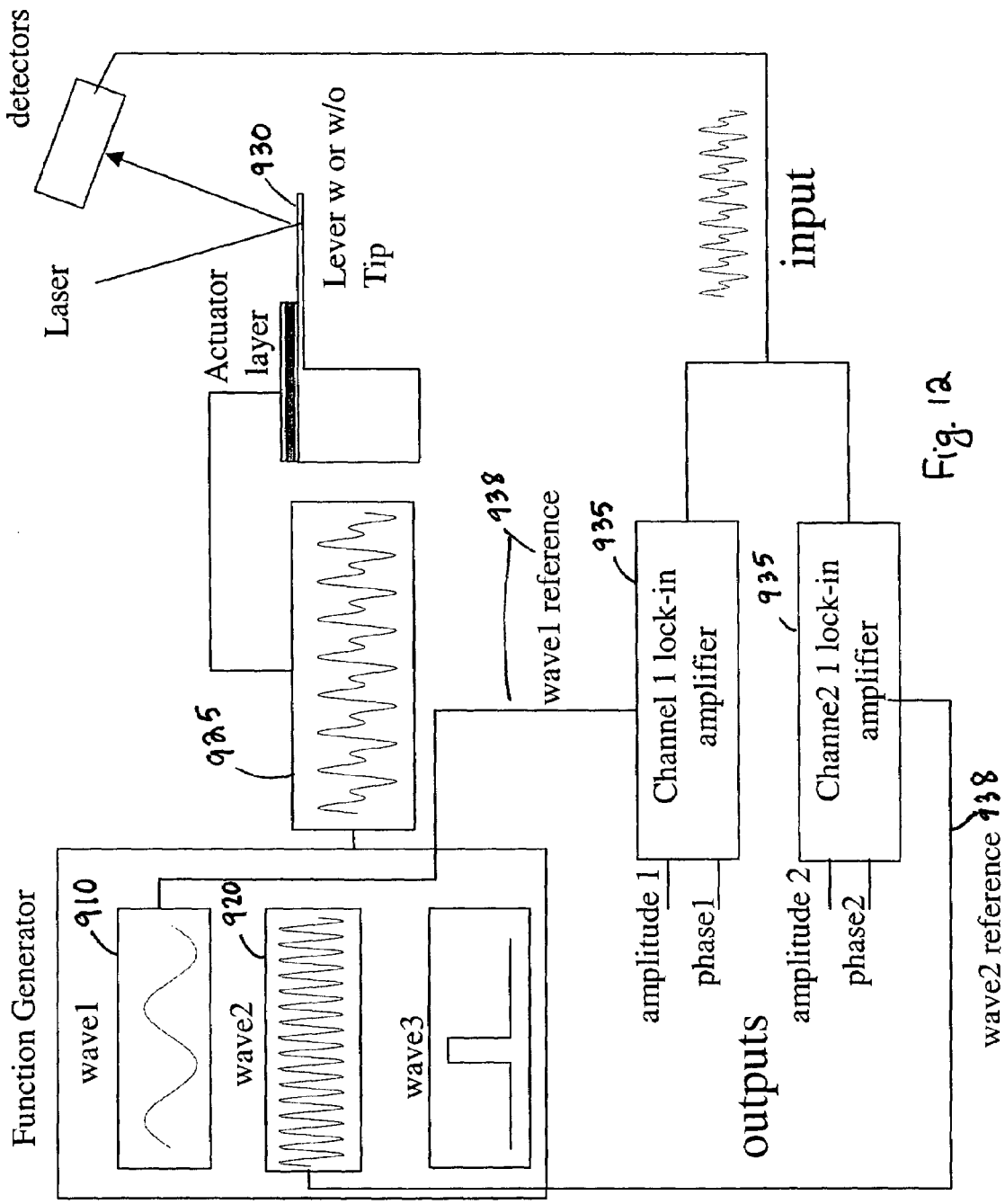
FIG. 12 shows a composed drive with superposition of multiple frequency components and multichannel lock-in amplifier which simultaneously decompose Fourier components of the corresponding reference frequency in the detected responses.

FIG. 12 represents an alternative embodiment of the drive signal generation and detection signal deconvolusion. The function generator 70 of FIG. 1 produces multiple sine waves, such as exemplified by, but not limited to, wave1 910 and wave2 920 having different frequencies as shown in FIG. 12. The multiple frequency waves are then superpositioned to form a combined drive wave 925. The combined drive wave 925 then excites an active lever 930. The same drive wave 925 is also sent to multiple channel lock-in amplifiers 935 to serve as a reference signal for the lock in amplifiers. The detection signal, which reflects the response of the sample or tip sample interaction as a result of the active lever deformation due to the superposition of waves (such as wave1+wave2+ . . . ) of different frequencies, is then sent to the lock-in amplifiers 935 with different references 938. The output amplitude and phase of the respective channels reflect material response in the frequency of the selected channel with the correspondent reference frequency. All the channels, two in the case exemplified in FIG. 12, produce the same pair of data for the corresponding reference frequencies. The advantage of the multichannel drive and analysis is that the multiple frequency data is acquired simultaneously, making it possible to scan the sample surfaces with the xy stage and map discrete frequency responses at all the locations of the sample. The wave components may also possibly include repetitive force pulses.

Figure 13:
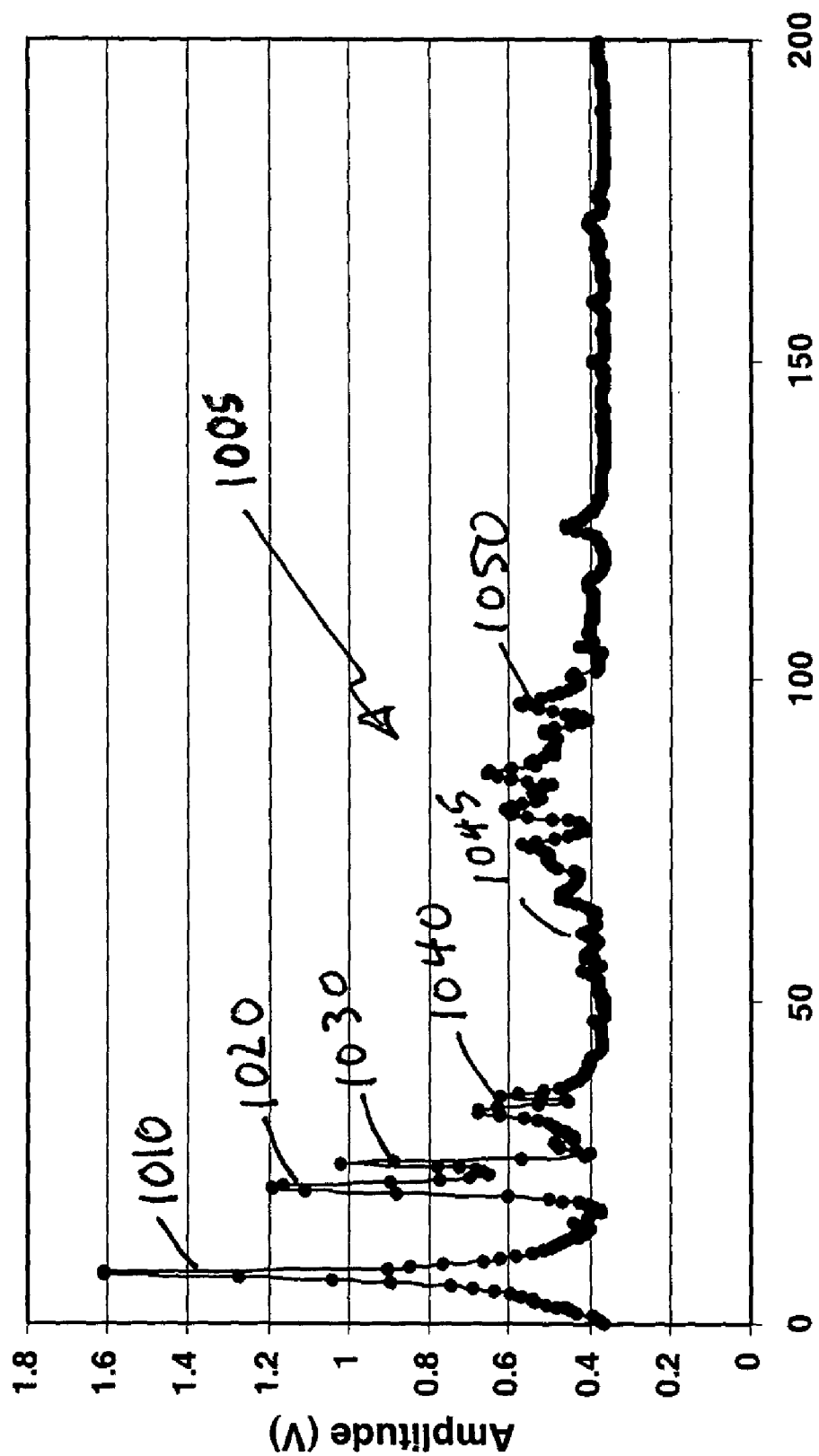
FIG. 13 is a graph showing the frequency versus amplitude response of a prior art scanning probe instrument actuated through the cantilever substrate.

FIG. 13 shows the amplitude versus frequency spectra from the prior art. In this technique, a piezo force modulation device (not shown) is coupled to the cantilever holder (not shown). The cantilever (not shown) is free oscillating in the sense that it is not interacting with the surface of any sample. Due to the substantial overdrive required to drive the microcantilever devices of the prior art into resonance, numerous resonance peaks associated with the surrounding mechanical environment is present in the spectra 1005, as exemplified, for example, in FIG. 13 as peaks 1010 thru 1050. Each peak shifts the phase by 180 degrees, regardless of the resonance peak height (not shown). Referring to FIGS. 1 and 13, when the tip 60 attached to the cantilever 20 is interacting with sample 50, the amplitude spectra 1045, including the resonance peaks, such as peaks 1010 thru 1050 for example, become the background of the tip-sample measurements and the material properties are nearly indistinguishable from the measurements, thereby rendering the phase spectra and the amplitude spectra of little value in determining the material properties of the sample.

Figure 14:
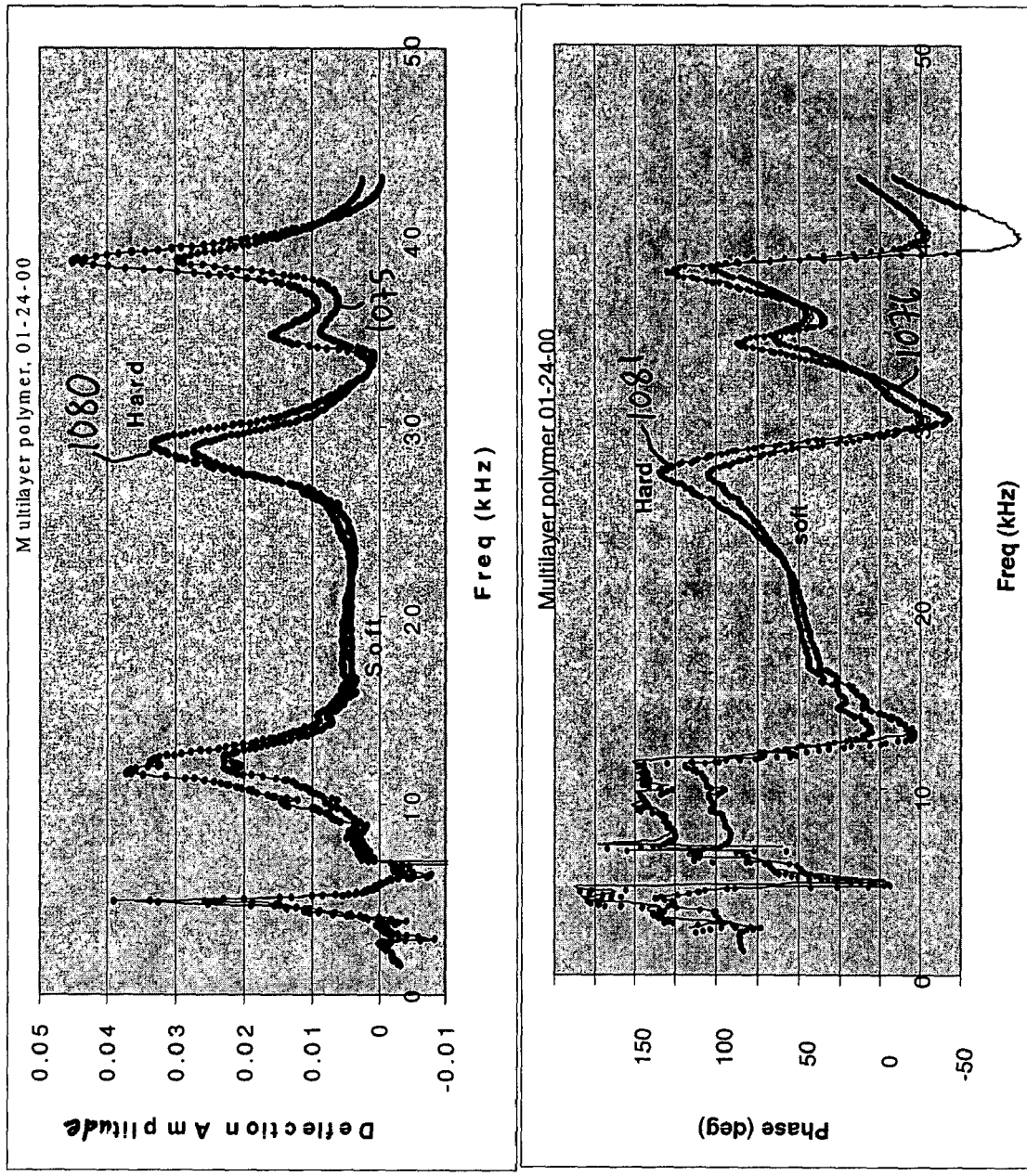
FIG. 14 is a graph showing the phase versus amplitude response of a prior art scanning probe instrument actuated through the cantilever substrate.

FIG. 14 is a graphic representation of the phase and amplitude spectra of a multilayered polyethylene (PE) sample as measured in accordance with the previous art by modulating the sample stage. The multilayered polyethylene sample is comprised of a sandwiched configuration of soft and hard polyethylene samples stacked in a direction perpendicular to the sample surface. Curve 1 1075 and Curve 2 1080 represent soft and hard PE sample amplitude responses as a function of frequency. Curve 1 1076 and Curve 2 1081 represent soft and hard PE sample phase response as a function of frequency. In all of these curves, the parasitic resonance of the holder or stage dominates the response, rendering material properties distinguishable only in individual frequencies and the judgment of the properties highly subjective.

Figure 15:
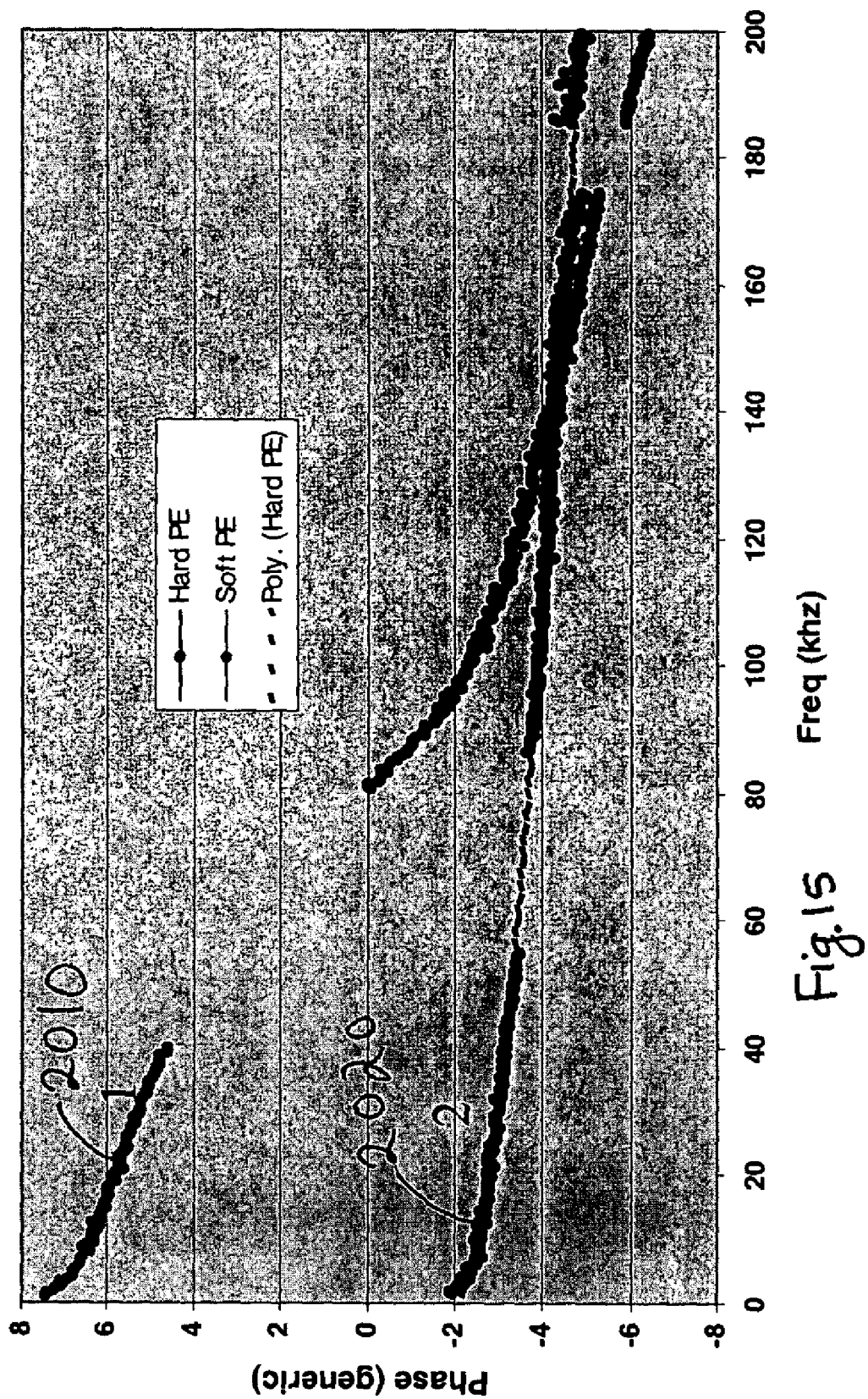
FIG. 15 graphical representation of phase versus frequency response of a scanning probe instrument acting on a multi-layer polyethylene sample with hard and soft layers.

FIG. 15 is a graphic representation of the phase spectra of a multilayered polyethylene (PE) sample as measured in accordance with the present invention. The same multilayered polyethylene sample, described in the above paragraph in connection with FIG. 14, is employed. The sample is comprised of a sandwiched configuration of soft and hard polyethylene samples stacked in a direction perpendicular to the sample surface. The spectral graph shown in FIG. 15 depicts the spectra of the soft polyethylene layer shown in Curve 1 2010, and the spectra of the hard polyethylene layer shown in Curve 2 2020. The mechanical spectra reflected in the phase-frequency plot clearly shows the difference of the materials and their dependencies on the frequency change. At higher frequency, soft polymer is unable to exhibit viscoelastic flow and behaves more or less like the hard material, a tendency generally observed in a bulk material.

Figure 16C:
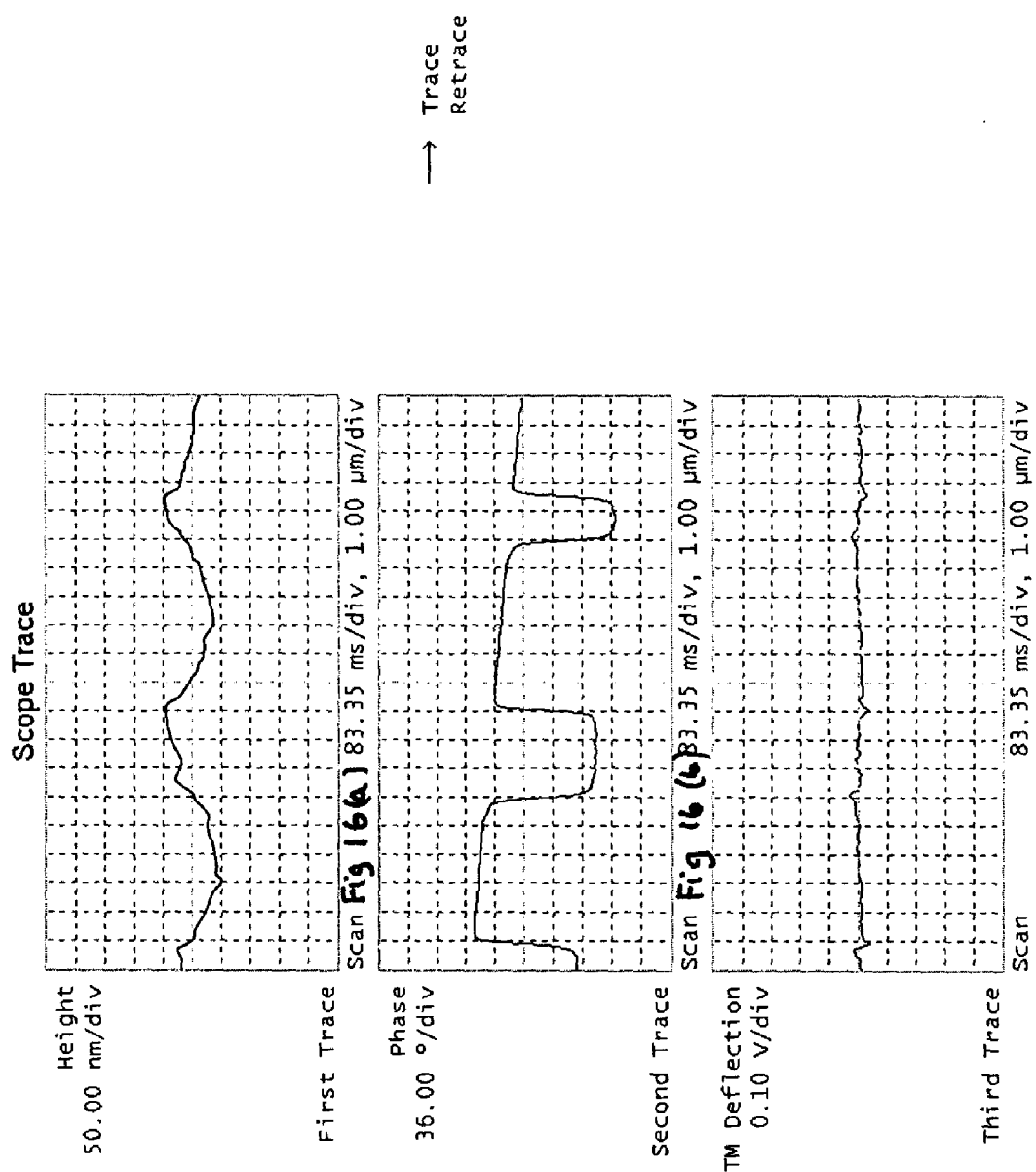

FIG. 16 is a graphic representation of the phase spectra obtained from the same multilayered PE as shown in FIGS. 14 and 15 and described above. In FIG. 16, the drive frequency is fixed but the tip is scanning different positions across the sample, which is a sandwich with hard and soft layers. FIG. 16a shows the height profile measured by maintaining constant DC deflection as the tip scans the surface of the sample. FIG. 16b reflects the phase difference of Curve 1 1081 and Curve 2 1076 in FIG. 14 at 10 khz. FIG. 16c is the deflection feedback control error. Again, the soft and hard PE clearly shows distinguishable phase spectra. The soft PE behaves more and more like the hard PE at higher frequencies, an observation consistent with the Maxwell model of the viscoelastic properties of polymer materials.

According to equations 1 and 2, the phase lag between soft and hard material is independent of deformation strain amplitude for linear viscoelasticity. The measurement of quality factor as a function of frequency is therefore independent of the contact area. In atomic force microscopy (AFM) measurement, the contact area of the a tip changes drastically with the topology of the sample surface. All property measurements in the prior art contain topographic information as a result of the contact interaction. However, the topographic contribution in the present invention is deduced on the basis of the phase lag, being independent of deformation strain amplitude for linear viscoelasticity. FIG. 16 illustrates this concept, in that the phase lag is independent of the topology and depends only on the material property. It will be appreciated that the mechanical spectra at this point of frequency depends only on the materials involved and has little to do with their surface topography.

Figure 17:
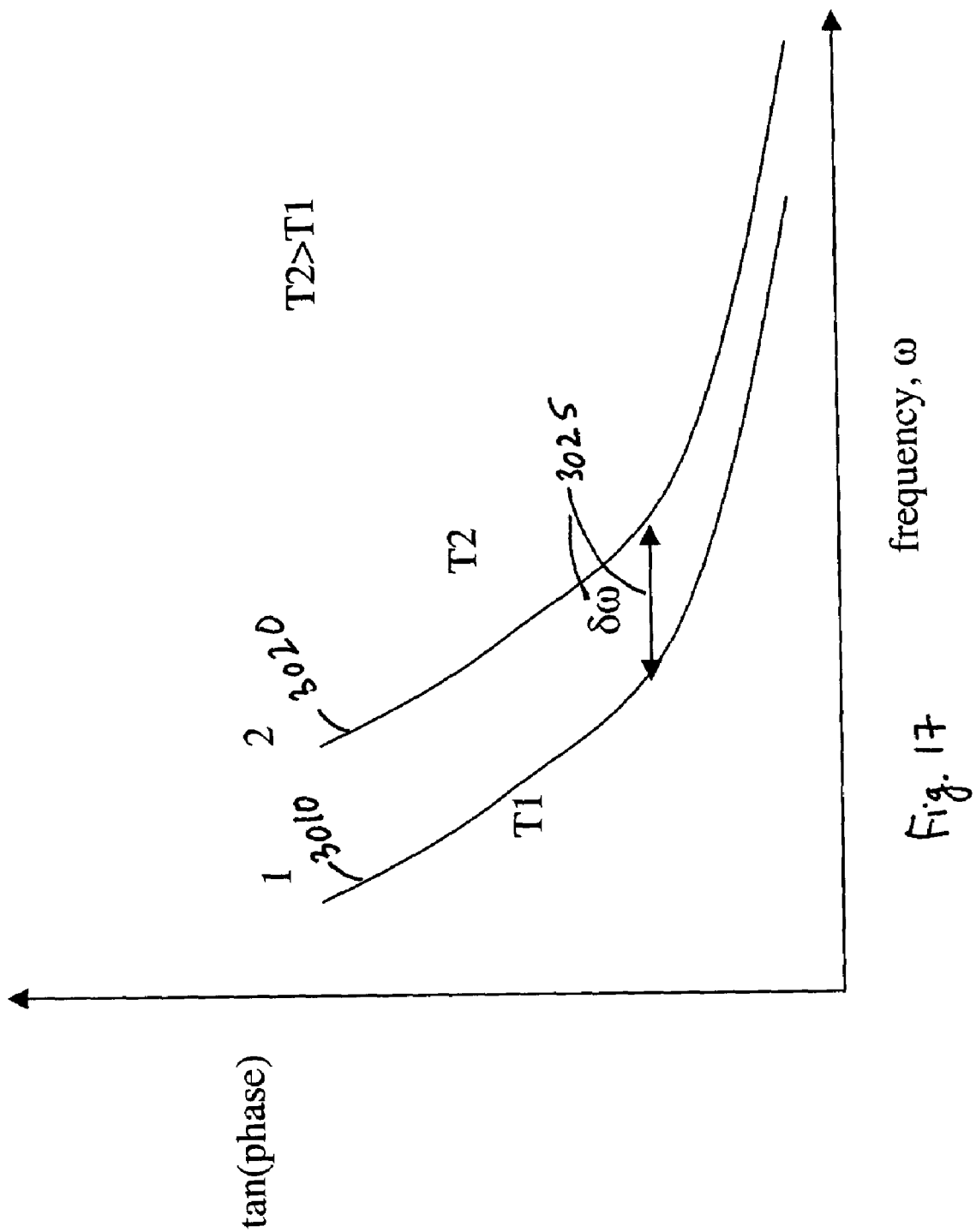
FIG. 17 illustrates the process of deriving activation energy.

FIG. 17 illustrates the measurement to determine activation energy of the present art. In the measurements, the probe is preloaded to interact with the sample according to the AFM control of the previous art, depicted in FIG. 3. The frequency sweep is then performed to measure the tip/surface response in a wide frequency range, yielding Curve 1 3010. The temperature of the sample is then increased using the art described in FIG. 11 to a temperature T2 and the frequency sweep is repeated again. The sweep phase data are displayed as Curve 1 3010 and Curve 2 3020 in FIG. 17. Due to temperature change, the curves will shift translationally along the frequency axis by an amount δω 3025. Using Arrhenius formula:

$$\ln(\omega 1/\omega 2) = \frac{H}{k} \cdot \frac{1}{T1^{-1} - T2^{-1}} \quad (7)$$

the activation energy H can be determined, where the parameters used in Eq. 7 above are as illustrated in FIG. 17 with k being the Boltzman constant.

Furthermore, the viscoelastic relaxation constant $\tau_i$ follows a thermal activation process defined by the relationship:

$$\tau_i = \tau_{0i} * \exp(-Hi/kT) \quad (8)$$

where τ represents the viscoelastic relaxation constant, $\tau_0$ is the attempt frequency of the thermal activation. H is the activation energy and T is temperature. (Details of the physical mechanism involved are explained in Anelastic Relaxation in Crystalline Solids, Nowick and Berry, Pergaman Press 1972). The relationship represented by Eq. 8, causes the spectra to shift horizontally as a function of frequency for measurements at different temperatures, as illustrated in FIG. 17. In FIG. 17, Curve 1 3010 and Curve 2 3020 represent phase change as a function of frequency for the same material but at different temperatures, T1 and T2. For linear viscoelasticity, Curve 2 3020 will shift horizontally a quantity of δω 3025 with respect to Curve 1 3010 as the temperature changes. The term δω 3025 can be used to derive the activation energy of the viscous flow.

The mechanical spectra can also be determined by driving the samples in FIGS. 7a and 7b into resonance and then withdrawing the drive force. The amplitude of the cantilever or sample oscillation will decrease in the shape of the free decay. The time constant of free decay is a direct measurement of mechanical quality factor of the sample itself or the sample interacting with a cantilever probe.

Although the preferred embodiment of the present invention has been described, it will be recognized that numerous changes and variations can be made and that the scope of the present invention is intended to be defined by the claims.

What is claimed:

1. A method of performing dynamic nanomechanical analysis of a sample comprising the steps of:
   providing a cantilever probe;
   interacting the cantilever probe with a sample by applying a force across a wide range of frequencies such that the applied force produces a phase response variation in the absence of contact of the tip with the sample that is less than ±10° over at least 10 kHz of the range of frequencies;
   detecting a motion of the cantilever probe in response to the applied force over the range of frequencies; and
   analyzing the motion of the cantilever probe over at least a portion of the range of frequencies to determine a mechanical response of the sample.

2. The method of claim 1, further comprising performing the steps at a plurality of positions with respect to the sample.

3. The method of claim 1, further comprising performing the steps at a plurality of temperatures.

4. The method of claim 1, further comprising performing the steps at a plurality of environmental conditions.

5. The method of claim 1, wherein the step of detecting the motion detects a value selected from the set consisting of: a motion of the cantilever probe, a motion of the sample, a deformation of the sample, or any combination thereof.

6. The method of claim 1, wherein the step of interacting the cantilever probe with the sample is performed by applying a preset force selected from the set including: a force applied in a DC mode, a force applied in an AC mode, or any combination thereof.

7. The method of claim 6, further an AC force that perturbs the preset force over a continuous wide frequency range.

8. The method of claim 1, wherein the step of detecting a motion detects a motion of both the cantilever probe and a deformation or motion of the sample.

9. The method of claim 1, wherein the step of analyzing is performed in terms of amplitude, phase and frequency of the cantilever probe and in terms of amplitude, phase and frequency of the sample.

10. The method of claim 8, wherein the step of analyzing is performed in terms of: a three-dimensional motion of the cantilever probe, a three-dimensional deformation of the sample, or a combination of both the motion of the cantilever probe and the deformation of the sample.

11. The method of claim 1, wherein the step of analyzing is performed in terms of amplitude, phase, and frequency.

12. The method of claim 1, wherein the step of analyzing is performed in terms of the free decay of the cantilever probe after the force is withdrawn.

13. The method of claim 1, further comprising choosing a tip of the cantilever probe from the group consisting of a stylus shaped tip and a ball shaped tip.

14. The method of claim 1, wherein the sample is provided in a deformable shape such that the step of interacting the cantilever probe is accomplished through contact of a probe tip to the deformable sample to cause deformation across the wide range of frequencies.

15. The method of claim 14, wherein the deformable shape is selected from the set consisting of: a secondary cantilever with at least one end fixed, a membrane, a bridge, or any combination thereof.

16. The method of claim 1, wherein the step of detecting is accomplished by a primary displacement transducer detecting the cantilever probe motion.

17. The method of claim 8, wherein the step of detecting is accomplished by a secondary displacement transducer detecting the motion and deformation of a deformable sample.

18. The method of claim 1, wherein the mechanical response includes a mechanical property of the sample that is selected from the set consisting of: mechanical quality, elasticity, viscoelasticity, or any combination thereof.

19. The method of claim 1, wherein the mechanical response includes a mechanical property of the sample that is selected from the set consisting of: mechanical quality, elasticity, viscoelasticity, or any combination thereof that is determined as a function of temperature, frequency or any combination thereof.

20. The method of claim 1, wherein the step of providing a cantilever probe includes providing a cantilever probe selected from the set including: a cantilever only and a cantilever with a tip operably attached to the cantilever.

21. The method of claim 1, wherein the step of providing the cantilever probe includes providing a cantilever probe with an active piezoelectric layer coated on at least a portion of a surface of the cantilever probe and the piezoelectric layer is utilized to apply the force in the step of interacting the cantilever probe with the sample in the range of frequencies.

22. The method of claim 1, wherein the force applied to the cantilever probe is an amount between $10^{-6}$ and 1000.0 micro Newtons.

23. The method of claim 1, wherein the step of interacting the cantilever probe with the sample is accomplished by applying the force through a combination of flexural and torsional deformation of the cantilever probe.

24. The method of claim 23, wherein the step of providing the cantilever probe includes providing a cantilever probe with an active piezoelectric layer coated on at least a portion of a surface of the cantilever probe and the piezoelectric layer is utilized to apply the force in the step of interacting the cantilever probe with the sample.

25. The method of claim 24, wherein the active piezoelectric layer comprises at least two symmetric strips positioned along an axis of the cantilever probe and wherein electrodes operably associated with each strip each receive a drive signal out of phase with any other drive signals to excite torsional deformation of the cantilever probe, and each electrode receives a drive signal in phase with the other drive signals to excite flexural deformation of the cantilever probe.

26. The method of claim 25, wherein a magnitude of the drive signal in-phase and out of phase drives to individual piezo elements is adjustable independently.

27. A method of performing dynamic nanomechanical analysis of a sample comprising the steps of:
   providing a cantilever probe;
   interacting the cantilever probe with a sample by applying a force across a wide range of frequencies such that the applied force produces a phase response variation in the absence of contact of the tip with the sample that is less than ±10° over at least 10 kHz of the range of frequencies;

detecting a motion of the cantilever probe in response to the applied force over the range of frequencies; and analyzing the motion of the cantilever probe over at least a portion of the range of frequencies to determine a mechanical response of the sample, wherein the step of analyzing is performed in temis of sample oscillation after the force is withdrawn in order to derive the mechanical response in terms of at least one of the following properties: elasticity, anelasticity, or viscoelasticity of the sample.

* * * * *